United States Patent
Clawson

(10) Patent No.: US 10,657,614 B2
(45) Date of Patent: May 19, 2020

(54) LOCATOR DIAGNOSTIC SYSTEM FOR EMERGENCY DISPATCH

(71) Applicant: Jeffrey J. Clawson, Salt Lake City, UT (US)

(72) Inventor: Jeffrey J. Clawson, Salt Lake City, UT (US)

( * ) Notice: Subject to any disclaimer, the term of this patent is extended or adjusted under 35 U.S.C. 154(b) by 53 days.

(21) Appl. No.: 14/757,797

(22) Filed: Dec. 23, 2015

(65) Prior Publication Data

US 2017/0187878 A1 Jun. 29, 2017

(51) Int. Cl.
*G06Q 50/26* (2012.01)
*H04M 3/51* (2006.01)
*A61B 5/00* (2006.01)

(52) U.S. Cl.
CPC .......... *G06Q 50/265* (2013.01); *A61B 5/747* (2013.01); *G06Q 50/26* (2013.01); *H04M 3/5116* (2013.01); *H04M 2242/04* (2013.01); *H04M 2242/30* (2013.01)

(58) Field of Classification Search
CPC ............ H04M 3/5116; H04M 2242/04; G06F 3/0484; G06Q 50/265; G06Q 50/26; A61B 5/747
See application file for complete search history.

(56) References Cited

U.S. PATENT DOCUMENTS

| | | | |
|---|---|---|---|
| 3,799,147 A | 3/1974 | Adolph et al. | |
| 4,130,881 A | 12/1978 | Haessler et al. | |
| 4,164,320 A | 8/1979 | Irazoqui et al. | |
| 4,237,344 A | 12/1980 | Moore | |
| 4,290,114 A | 9/1981 | Sinay | |
| 4,338,493 A | 7/1982 | Stenhuis et al. | |
| 4,360,345 A | 11/1982 | Hon | |

(Continued)

FOREIGN PATENT DOCUMENTS

| CN | 1674685 A | 9/2005 |
|---|---|---|
| CN | 101169840 A | 4/2008 |

(Continued)

OTHER PUBLICATIONS

Associated Press, The *Simpson* Murder Case; Nicole Simpson's 911 Calls, The Los Angeles Times (Jun. 23, 1994) (Year: 1994).*

(Continued)

*Primary Examiner* — Justin R. Blaufeld
(74) *Attorney, Agent, or Firm* — Stoel Rives LLP

(57) ABSTRACT

Systems and methods are provided to guide an emergency dispatcher in responding to emergency calls where the incident location is not known. The systems and methods can include a locator diagnostic tool configured to facilitate thorough and consistent information gathering for calls where the incident location is not known. The locator diagnostic tool may traverse a logical tree configured to gather information that can aid in identifying the incident location and/or provide instructions to the caller that may allow the incident location to be identified. For example, the locator diagnostic tool may aid callers in locating devices designed to transmit their location. The locator diagnostic tool may traverse different logical paths depending on if the caller can speak freely or not, depending on if the caller or a third party is missing, and/or depending on the type of caller location (e.g., inside, outside, or underground).

23 Claims, 24 Drawing Sheets

(56) References Cited

U.S. PATENT DOCUMENTS

| | | | |
|---|---|---|---|
| 4,455,548 | A | 6/1984 | Burnett |
| 4,489,387 | A | 12/1984 | Lamb et al. |
| 4,731,725 | A | 3/1988 | Suto et al. |
| 4,839,822 | A | 6/1989 | Dormond et al. |
| 4,858,121 | A | 8/1989 | Barber et al. |
| 4,865,549 | A | 9/1989 | Sonsteby |
| 4,922,514 | A | 5/1990 | Bergeron et al. |
| 4,926,495 | A | 5/1990 | Comroe et al. |
| 4,945,476 | A | 7/1990 | Bodick et al. |
| 4,967,754 | A | 11/1990 | Rossi |
| 5,063,522 | A | 11/1991 | Winters |
| 5,065,315 | A | 11/1991 | Garcia |
| 5,072,383 | A | 12/1991 | Brimm et al. |
| 5,077,666 | A | 12/1991 | Brimm et al. |
| 5,086,391 | A | 2/1992 | Chambers |
| 5,109,399 | A | 4/1992 | Thompson |
| 5,122,959 | A | 6/1992 | Nathanson et al. |
| 5,193,855 | A | 3/1993 | Shamos |
| 5,228,449 | A | 7/1993 | Christ et al. |
| 5,253,164 | A | 10/1993 | Holloway et al. |
| 5,255,187 | A | 10/1993 | Sorensen |
| 5,291,399 | A | 3/1994 | Chaco |
| 5,323,444 | A | 6/1994 | Ertz et al. |
| 5,339,351 | A | 8/1994 | Hoskinson et al. |
| 5,348,008 | A | 9/1994 | Bornn et al. |
| 5,379,337 | A | 1/1995 | Castillo et al. |
| 5,404,292 | A | 4/1995 | Hendrickson |
| 5,410,471 | A | 4/1995 | Alyfuku et al. |
| 5,423,061 | A | 6/1995 | Fumarolo et al. |
| 5,438,996 | A | 8/1995 | Kemper et al. |
| 5,441,047 | A | 8/1995 | David et al. |
| 5,462,051 | A | 10/1995 | Oka et al. |
| 5,471,382 | A | 11/1995 | Tallman et al. |
| 5,502,726 | A | 3/1996 | Fischer |
| 5,513,993 | A | 5/1996 | Lindley et al. |
| 5,516,702 | A | 5/1996 | Senyei et al. |
| 5,521,812 | A | 5/1996 | Feder et al. |
| 5,536,084 | A | 7/1996 | Curtis et al. |
| 5,544,649 | A | 8/1996 | David et al. |
| 5,554,031 | A | 9/1996 | Moir et al. |
| 5,590,269 | A | 12/1996 | Kruse et al. |
| 5,593,426 | A | 1/1997 | Morgan et al. |
| 5,594,638 | A | 1/1997 | Iliff |
| 5,594,786 | A | 1/1997 | Chaco et al. |
| 5,596,994 | A | 1/1997 | Bro |
| 5,630,125 | A | 5/1997 | Zellweger |
| 5,636,873 | A | 6/1997 | Sonsteby |
| 5,650,995 | A | 7/1997 | Kent |
| 5,660,176 | A | 8/1997 | Iliff |
| 5,675,372 | A | 10/1997 | Aguayo, Jr. et al. |
| 5,682,419 | A | 10/1997 | Grube et al. |
| 5,684,860 | A | 11/1997 | Milani et al. |
| 5,689,229 | A | 11/1997 | Chaco et al. |
| 5,719,918 | A | 2/1998 | Serbetciouglu et al. |
| 5,722,418 | A | 3/1998 | Bro |
| 5,724,983 | A | 3/1998 | Selker et al. |
| 5,734,706 | A | 3/1998 | Windsor et al. |
| 5,745,532 | A | 4/1998 | Campana, Jr. |
| 5,748,907 | A | 5/1998 | Crane |
| 5,754,960 | A | 5/1998 | Downs et al. |
| 5,759,044 | A | 6/1998 | Redmond |
| 5,761,278 | A | 6/1998 | Pickett et al. |
| 5,761,493 | A | 6/1998 | Blakeley et al. |
| 5,764,923 | A | 6/1998 | Tallman et al. |
| 5,787,429 | A | 7/1998 | Nikolin, Jr. |
| 5,805,670 | A | 9/1998 | Pons et al. |
| 5,809,493 | A | 9/1998 | Ahamed et al. |
| 5,822,544 | A | 10/1998 | Chaco et al. |
| 5,823,948 | A | 10/1998 | Ross, Jr. et al. |
| 5,826,077 | A | 10/1998 | Blakeley et al. |
| 5,832,187 | A | 11/1998 | Pedersen et al. |
| 5,842,173 | A | 11/1998 | Strum et al. |
| 5,844,817 | A | 12/1998 | Lobley et al. |
| 5,850,611 | A | 12/1998 | Krebs |
| 5,857,966 | A | 1/1999 | Clawson |
| 5,901,214 | A | 5/1999 | Shaffer et al. |
| 5,902,234 | A | 5/1999 | Webb |
| 5,910,987 | A | 6/1999 | Ginter et al. |
| 5,912,818 | A | 6/1999 | McGrady et al. |
| 5,915,019 | A | 6/1999 | Ginter et al. |
| 5,926,526 | A | 7/1999 | Rapaport et al. |
| 5,933,780 | A | 8/1999 | Connor et al. |
| 5,961,446 | A | 10/1999 | Beller et al. |
| 5,962,891 | A | 10/1999 | Arai |
| 5,964,700 | A | 10/1999 | Tallman et al. |
| 5,986,543 | A | 11/1999 | Johnson |
| 5,989,187 | A | 11/1999 | Clawson |
| 5,991,730 | A | 11/1999 | Lubin et al. |
| 5,991,751 | A | 11/1999 | Rivette et al. |
| 6,004,266 | A | 12/1999 | Clawson |
| 6,010,451 | A | 1/2000 | Clawson |
| 6,022,315 | A | 2/2000 | Iliff |
| 6,035,187 | A | 3/2000 | Franza |
| 6,040,770 | A | 3/2000 | Britton |
| 6,052,574 | A | 4/2000 | Smith, Jr. |
| 6,053,864 | A | 4/2000 | Clawson |
| 6,058,179 | A | 5/2000 | Shaffer et al. |
| 6,074,345 | A | 6/2000 | van Oostrom et al. |
| 6,076,065 | A | 6/2000 | Clawson |
| 6,078,894 | A | 6/2000 | Clawson et al. |
| 6,084,510 | A | 7/2000 | Lemelson et al. |
| 6,106,459 | A | 8/2000 | Clawson |
| 6,112,083 | A | 8/2000 | Sweet et al. |
| 6,115,646 | A | 9/2000 | Fiszman et al. |
| 6,117,073 | A | 9/2000 | Jones et al. |
| 6,118,866 | A | 9/2000 | Shtivelman |
| 6,127,975 | A | 10/2000 | Maloney |
| 6,134,105 | A | 10/2000 | Lueker |
| 6,292,542 | B1 | 9/2001 | Bilder |
| 6,370,234 | B1 | 4/2002 | Kroll |
| 6,535,121 | B2 | 3/2003 | Matheny |
| 6,594,634 | B1 | 7/2003 | Hampton et al. |
| 6,607,481 | B1 | 8/2003 | Clawson |
| 6,610,012 | B2 | 8/2003 | Mault |
| 6,696,956 | B1 | 2/2004 | Uchida et al. |
| 6,710,711 | B2 | 3/2004 | Berry |
| 6,771,163 | B2 | 8/2004 | Linnett et al. |
| 6,879,819 | B2 | 4/2005 | Brooks |
| 6,901,397 | B1 | 5/2005 | Moldenhauer et al. |
| 6,931,112 | B1 | 8/2005 | McFarland et al. |
| 6,968,375 | B1 | 11/2005 | Brown |
| 7,043,262 | B2 | 5/2006 | Nageli |
| 7,106,835 | B2 | 9/2006 | Saalsaa |
| 7,194,395 | B2 | 3/2007 | Genovese |
| 7,289,944 | B1 | 10/2007 | Genovese |
| 7,428,301 | B1 | 9/2008 | Clawson |
| 7,436,937 | B2 | 10/2008 | Clawson |
| 7,438,301 | B2 | 10/2008 | Schilling et al. |
| 7,645,234 | B2 | 1/2010 | Clawson |
| 7,703,020 | B2 | 4/2010 | Bhattaru |
| 7,783,586 | B2 | 8/2010 | Friedlander et al. |
| 7,978,826 | B2 | 7/2011 | Salafia et al. |
| 8,066,638 | B2 | 11/2011 | Clawson |
| 8,081,951 | B1 | 12/2011 | Blum |
| 8,103,523 | B2 | 1/2012 | Clawson |
| 8,294,570 | B2 | 10/2012 | Clawson |
| 8,335,298 | B2 | 12/2012 | Clawson |
| 8,346,942 | B2 | 1/2013 | Ezerzer et al. |
| 8,355,483 | B2 | 1/2013 | Clawson |
| 8,396,191 | B2 | 3/2013 | Clawson |
| 8,417,533 | B2 | 4/2013 | Clawson |
| 8,462,914 | B2 | 6/2013 | Ragno et al. |
| 8,488,748 | B2 | 7/2013 | Clawson |
| 8,494,868 | B2 | 7/2013 | Saalsaa |
| 8,538,374 | B1 | 9/2013 | Haimo et al. |
| 8,670,526 | B2 | 3/2014 | Clawson |
| 8,712,020 | B2 | 4/2014 | Clawson |
| 8,873,719 | B2 | 10/2014 | Clawson |
| 8,971,501 | B2 | 3/2015 | Clawson et al. |
| 9,319,859 | B2 | 4/2016 | Clawson |
| 9,875,514 | B2 | 1/2018 | Smallwood |
| 9,877,171 | B2 | 1/2018 | Clawson |
| 2002/0004729 | A1 | 1/2002 | Zak et al. |

(56) References Cited

U.S. PATENT DOCUMENTS

| | | |
|---|---|---|
| 2002/0022492 A1* | 2/2002 | Barak .................. H04M 3/4228 455/457 |
| 2002/0106059 A1 | 8/2002 | Kroll et al. |
| 2003/0025602 A1 | 2/2003 | Medema et al. |
| 2003/0028536 A1 | 2/2003 | Singh et al. |
| 2003/0050538 A1 | 3/2003 | Naghavi et al. |
| 2003/0179862 A1* | 9/2003 | Sierra ................ H04M 3/42229 379/88.01 |
| 2003/0187615 A1 | 10/2003 | Epler |
| 2003/0195394 A1 | 10/2003 | Saalsaa |
| 2003/0211856 A1 | 11/2003 | Zilliacus |
| 2003/0212575 A1 | 11/2003 | Saalsaa et al. |
| 2004/0219927 A1* | 11/2004 | Sumner ................ G01S 5/0221 455/456.1 |
| 2005/0015115 A1 | 1/2005 | Sullivan et al. |
| 2005/0065813 A1 | 3/2005 | Mishelevich et al. |
| 2006/0031097 A1 | 2/2006 | Lipscher |
| 2006/0038674 A1 | 2/2006 | Sumcad et al. |
| 2006/0059423 A1 | 3/2006 | Lehmann et al. |
| 2006/0122520 A1 | 6/2006 | Banet et al. |
| 2006/0152372 A1 | 7/2006 | Stout |
| 2006/0167346 A1 | 7/2006 | Sarel |
| 2006/0173500 A1 | 8/2006 | Walker et al. |
| 2006/0178908 A1 | 8/2006 | Rappaport |
| 2006/0212315 A1 | 9/2006 | Wiggins |
| 2006/0225213 A1 | 10/2006 | Tomcany |
| 2007/0055559 A1 | 3/2007 | Clawson |
| 2007/0111702 A1 | 5/2007 | Sanzelius et al. |
| 2007/0112275 A1 | 5/2007 | Cooke et al. |
| 2007/0116189 A1 | 5/2007 | Clawson |
| 2007/0189480 A1 | 8/2007 | Salafia et al. |
| 2007/0201664 A1 | 8/2007 | Salafia et al. |
| 2008/0208801 A1 | 8/2008 | Friedlander et al. |
| 2008/0310600 A1 | 12/2008 | Clawson |
| 2009/0037374 A1 | 2/2009 | Delia et al. |
| 2009/0067585 A1 | 3/2009 | Clawson |
| 2009/0168975 A1 | 7/2009 | Clawson |
| 2009/0179756 A1 | 7/2009 | Stout |
| 2009/0191529 A1 | 7/2009 | Mozingo et al. |
| 2009/0233631 A1 | 9/2009 | Butler, Sr. et al. |
| 2009/0276489 A1 | 11/2009 | Ragno et al. |
| 2010/0004710 A1 | 1/2010 | Kellum |
| 2010/0088135 A1* | 4/2010 | Nielsen .................. G06Q 10/06 705/7.38 |
| 2010/0121156 A1 | 5/2010 | Yoo |
| 2010/0152800 A1 | 6/2010 | Walker et al. |
| 2010/0198755 A1 | 8/2010 | Soll et al. |
| 2010/0257250 A1 | 10/2010 | Salafia et al. |
| 2011/0050417 A1 | 3/2011 | Piccioni |
| 2011/0064204 A1 | 3/2011 | Clawson |
| 2011/0066002 A1 | 3/2011 | Clawson |
| 2011/0099031 A1 | 4/2011 | Nair |
| 2011/0205052 A1 | 8/2011 | Clawson |
| 2011/0215930 A1 | 9/2011 | Lee |
| 2012/0034897 A1 | 2/2012 | Kreitzer et al. |
| 2012/0066345 A1 | 3/2012 | Rayan et al. |
| 2012/0171989 A1 | 7/2012 | Matsuo et al. |
| 2012/0183128 A1 | 7/2012 | Clawson |
| 2012/0207286 A1 | 8/2012 | Clawson |
| 2012/0210271 A1 | 8/2012 | Clawson |
| 2013/0100268 A1 | 4/2013 | Mihailidis et al. |
| 2014/0031885 A1 | 1/2014 | Elghazzawi et al. |
| 2014/0064462 A1 | 3/2014 | Clawson |
| 2014/0211927 A1* | 7/2014 | Clawson ................ H04M 3/493 379/45 |
| 2014/0213212 A1 | 7/2014 | Clawson |
| 2014/0243749 A1 | 8/2014 | Edwards et al. |
| 2015/0289121 A1 | 10/2015 | Lesage et al. |
| 2015/0289122 A1 | 10/2015 | Friesen |
| 2016/0088455 A1 | 3/2016 | Bozik et al. |
| 2016/0148490 A1 | 5/2016 | Barnes et al. |
| 2016/0212605 A1 | 7/2016 | Clawson |
| 2016/0302050 A1* | 10/2016 | Blando .................. H04W 4/90 |
| 2016/0309026 A1* | 10/2016 | Sterman ................ H04M 3/5116 |
| 2016/0352898 A1 | 12/2016 | Clawson |
| 2017/0028767 A1 | 2/2017 | Tiberius |
| 2017/0262614 A1 | 9/2017 | Vishnubhatla et al. |
| 2017/0295477 A1 | 10/2017 | Clawson |
| 2018/0053401 A1 | 2/2018 | Martin et al. |
| 2019/0313230 A1 | 10/2019 | MacGabann |
| 2019/0318290 A1 | 10/2019 | Clawson et al. |
| 2019/0325726 A1 | 10/2019 | Clawson |
| 2019/0378397 A1 | 12/2019 | Williams, II et al. |

FOREIGN PATENT DOCUMENTS

| | | | |
|---|---|---|---|
| CN | 201117055 Y | 9/2008 | |
| CN | 102714524 A | 10/2012 | |
| EP | 2476092 A1 | 3/2011 | |
| GB | 2471960 | 1/2011 | |
| GB | 2478171 A | 8/2011 | |
| GB | 2482741 A | 2/2012 | |
| GB | 2489875 A | 10/2012 | |
| JP | 2002-049693 | 2/2002 | |
| JP | 2003-109162 A | 4/2003 | |
| JP | 2003111735 A * | 4/2003 | |
| JP | 2003-187003 A | 7/2003 | |
| JP | 2003-256963 A | 12/2003 | |
| JP | 2010-033201 A | 12/2010 | |
| KR | 10-2005-0085778 | 8/2005 | |
| KR | 10-2006-0084866 | 7/2006 | |
| KR | 2007-0043337 A | 4/2007 | |
| KR | 10-2008-0004125 | 1/2008 | |
| KR | 10-2009-0014837 A | 2/2009 | |
| WO | WO2004/030259 | 4/2004 | |
| WO | WO 2005/039406 A1 | 5/2005 | |
| WO | WO2006/015229 A2 | 2/2006 | |
| WO | 2007121237 | 10/2007 | |
| WO | WO-2007121237 A2 * | 10/2007 | .......... H04M 3/5116 |
| WO | WO 2008/014398 A2 | 1/2008 | |
| WO | WO2008/156876 A1 | 12/2008 | |
| WO | 2010101580 | 9/2010 | |
| WO | 2010120321 | 10/2010 | |
| WO | 2011031382 | 3/2011 | |
| WO | 2011031383 A1 | 3/2011 | |
| WO | WO2011/031383 | 3/2011 | |
| WO | 2011106036 | 9/2011 | |
| WO | 2012100052 | 7/2012 | |
| WO | 2012108897 | 8/2012 | |
| WO | WO2012/108898 A1 | 8/2012 | |
| WO | 2014039228 | 3/2014 | |
| WO | 2014120428 | 8/2014 | |
| WO | 2014121010 | 8/2014 | |
| WO | 2016109855 | 7/2016 | |
| WO | 2016190962 | 12/2016 | |
| WO | 2017112392 | 6/2017 | |
| WO | 2017176417 | 10/2017 | |
| WO | 2019200019 | 10/2019 | |
| WO | 2019204746 | 10/2019 | |

OTHER PUBLICATIONS

Hawai'i Police Department, Proper Use of 911, https://www.hawaiipolice.com/dispatch-911 (Feb. 6, 2015) (Year: 2015).*
Non-Final Office Action for U.S. Appl. No. 14/723,947, filed May 28, 2015, and mailed from the USPTO dated Mar. 31, 2016, 33 pgs.
Office Action Summary from USPTO for U.S. Appl. No. 10/140,635 dated Jul. 16, 2004, 11 pgs.
Office Action Summary from USPTO for U.S. Appl. No. 10/140,635 dated Apr. 19, 2005, 11 pgs.
Office Action Summary from USPTO for U.S. Appl. No. 10/140,635 dated Jan. 17, 2006, 13 pgs.
Office Action Summary from USPTO for U.S. Appl. No. 10/140,635 dated Sep. 20, 2006, 15 pgs.
Office Action Summary from USPTO for U.S. Appl. No. 10/140,635 dated Jun. 21, 2007, 15 pgs.
International Search Report for PCT/US2008/054987 filed on Feb. 26, 2008, and dated Oct. 8, 2008, 2 pgs.
Written Opinion of the International Searching Authority for PCT/US2008/054987 filed on Feb. 26, 2008, and dated Oct. 8, 2008, 9 pgs.

(56) References Cited

OTHER PUBLICATIONS

Notification of Transmittal of the International Search Report (2 pgs.) for PCT/US2009/040909, International Search Report, (2 pgs.), and Written Opinion (8 pgs.) mailed from International Searching Authority dated Jun. 10, 2009.
International Search Report and Written Opinion for PCT/US09/48577, International filing date Jun. 25, 2009, mailed from ISA dated Aug. 7, 2009, 9 pgs.
International Search Report and Written Opinion dated Jan. 19, 2011 in PCT Application No. PCT/US2010/043308, filed Jul. 27, 2010.
International Search Report and Written Opinion dated Jan. 19, 2011 in PCT Application No. PCT/US2010/043311, filed Jul. 27, 2010.
Office Action Summary from USPTO for U.S. Appl. No. 12/396,201 dated Mar. 8, 2011, 23 pgs.
International Search Report and Written Opinion PCT/US2010/050402, filed on Sep. 27, 2010, and mailed from ISA dated Apr. 27, 2011, 9 pgs.
Office Action Summary from USPTO for U.S. Appl. No. 12/268,963 dated Jul. 29, 2011, 18 pgs.
International Preliminary Report of Patentability for PCT/US2009/048577 filed on Jun. 25, 2009 dated Oct. 27, 2011, 7 pgs.
International Search Report and Written Opinion for PCT/US2011/042543 filed on Jun. 30, 2011, mailed from ISA dated Feb. 9, 2012, 11 pgs.
International Search Report and Written Opinion for PCT/US2011/042582 filed on Jun. 30, 2011, mailed from ISA dated Feb. 9, 2012, 8 pgs.
International Preliminary Report of Patentability for PCT/US2010/043308 filed on Jul. 27, 2010 dated Mar. 22, 2012, 6 pgs.
International Preliminary Report of Patentability for PCT/US2010/043311 filed on Jul. 27, 2010 dated Mar. 29, 2012, 6 pgs.
Office Action Summary from USPTO for U.S. Appl. No. 12/558,045 dated Mar. 22, 2012, 9 pgs.
Office Action Summary from USPTO for U.S. Appl. No. 12/558,808 dated Apr. 23, 2012, 9 pgs.
Office Action Summary from USPTO for U.S. Appl. No. 12/422,561 dated Jul. 3, 2012, 21 pgs.
International Search Report and Written Opinion for PCT/US2012/021867 filed on Jan. 19, 2012, and mailed from ISA dated Aug. 30, 2012, 8 pgs.
Office Action Summary from USPTO for U.S. Appl. No. 13/354,116 dated Jan. 22, 2013, 9 pgs.
Office Action Summary from USPTO for U.S. Appl. No. 12/422,561 dated Feb. 1, 2013, 26 pgs.
Notice of Allowance from USPTO for U.S. Appl. No. 13/026,055 dated Jan. 24, 2013.
Notice of Allowance from USPTO for U.S. Appl. No. 10/255,901 dated Feb. 20, 2013.
Nordberg, Marie, "Dispatch Disasters," Emergency Medicine, Aug. 1995.
Notice of Allowance from USPTO for U.S. Appl. No. 13/354,116 dated Jun. 7, 2013.
Liferidge, Aisha T., et al., "Ability of Laypersons to Use the Cincinnati Prehospital Stroke Scale", Prehospital Emergency Care, Elsevier, vol. 8, No. 4, Oct. 1, 2004, pp. 384-387.
Office Action Summary from USPTO for U.S. Appl. No. 13/026,043 dated Oct. 10, 2013.
International Preliminary Report of Patentability for PCT/US2011/042543 filed on Jun. 30, 2011 dated Aug. 22, 2013, 7 pgs.
International Preliminary Report of Patentability for PCT/US2011/042582 filed on Jun. 30, 2011 dated Aug. 22, 2013, 5 pgs.
Office Action Summary from USPTO for U.S. Appl. No. 13/605,501 dated Nov. 18, 2013.
International Search Report and Written Opinion for PCT/US2013/055537 filed on Aug. 19, 2013 and mailed from ISA dated Nov. 22, 2013.
Notice of Allowance from USPTO for U.S. Appl. No. 13/026,043 dated Jan. 13, 2014.
Nor, A. Mohd, et al., "Agreement Between Ambulance Paramedic- and Physician-Recorded Neurological Signs With Face Arm Speech Test (FAST) in Acute Stroke Patients", http://stroke.ahajournals.org/content/35/6/1355, Apr. 29, 2004, visited Nov. 17, 2013, 3 pgs.
Clark University "Active Shooter Emergency Plan" Revised Jan. 11, 2013.
Notice of Allowance from USPTO for U.S. Appl. No. 13/605,501 dated Mar. 6, 2014.
International Search Report and Written Opinion for PCT/US2014/011405 filed on Jan. 14, 2014 and mailed from ISA dated Apr. 25, 2014.
International Search Report and Written Opinion for PCT/US2014/014029 filed on Jan. 31, 2014 and mailed from ISA dated May 16, 2014.
Office Action Summary from USPTO for U.S. Appl. No. 13/755,793 dated Jul. 21, 2014.
International Preliminary Report of Patentability for PCT/US2013/055537 filed on Aug. 19, 2013 dated Mar. 19, 2015.
Notice of Allowance from USPTO for U.S. Appl. No. 12/422,561 dated Dec. 9, 2014.
Notice of Allowance from USPTO for U.S. Appl. No. 13/755,793 dated Sep. 22, 2014.
Non-Final Office Action for U.S. Appl. No. 14/169,302, filed Jan. 31, 2014, and mailed from the USPTO dated Sep. 25, 2015, 46 pgs.
Non-Final Office Action for U.S. Appl. No. 15/083,810, filed Mar. 29, 2016, and mailed from the USPTO dated Jul. 15, 2016, 28 pgs.
Notice of Allowance and Fee(s) Due for U.S. Appl. No. 14/723,947, filed May 28, 2015, and mailed from the USPTO dated Oct. 24, 2016, 29 pgs.
Peck, "Got a Minute? You Could Diagnose a Stroke," *WebMD Health News*, http://www.webmd.com/stroke/news/20030213/got-minute-you-could-diagnosie-stroke, Feb. 13, 2003, 3 pgs.
International Search Report and Written Opinion for Application No. PCT/US2016/064719 filed Dec. 2, 2016, and mailed from the International Searching Authority dated Feb. 16, 2017, 16 pgs.
Radosevich, Lynda, "Network holds sway on life, death," Computerworld, v27 n21, May 24, 1993, 2 pgs.
Harris, Roger, "Updated 911 Phone System Top Concern of Residents," Business First—Louisville, v9 n19 s1, Dec. 1992, 3 pgs.
"Geac Completes Software Install," Wireless Week, Nov. 18, 1996, 3 pgs.
"Dictaphone introduces Windows-based Computer-Aided Dispatch (CAD) system," Business Wire, Apr. 23, 1996, 2 pgs. (in commercial use in 1995).
Holroyd, Brian, et al., "Medical Control; Quality Assurance in Prehospital Care," JAMA, the Journal of American Medical Association, v256, n8, Aug. 1986, p. 1027-1031.
CBS web page News Story entitled "911 Operator: 'It's got to be Hell'", Mar. 31, 2006 (excerpts from 911 operators' actions during the attacks on Sep. 11, 2001), 3 pgs.
Best, Wendy, "999 United Emergency services share life-saving Role to boost response," Western Daily Press, WDP Severnside ed., May 27, 1999, 2 pgs.
Poellmitz, William C., "Wireless technology keeps public safety a step ahead," Nation's Cities Weekly, v21 n17, Apr. 27, 1998, 3 pgs.
Crowley, Mark, "Learning from CAD System Implementation," Communications, v29 n8, Aug. 1992, 5 pgs.
Anonymous, "Suburban Chicago towns centralize 911 services," Communications News, v31 n10, Oct. 1994, 2 pgs.
Office Action Summary from USPTO for U.S. Appl. No. 10/255,901 dated Dec. 31, 2003, 8 pgs.
Office Action Summary from USPTO for U.S. Appl. No. 10/255,901 dated Oct. 13, 2004, 8 pgs.
Office Action Summary from USPTO for U.S. Appl. No. 10/255,901 dated Jun. 29, 2005, 7 pgs.
Advisory Action Before the Filing of an Appeal Brief from USPTO for U.S. Appl. No. 10/255,901 dated Feb. 14, 2006, 3 pgs.
Office Action Summary from USPTO for U.S. Appl. No. 10/255,901 dated Jun. 7, 2006, 8 pgs.
Office Action Summary from USPTO for U.S. Appl. No. 10/255,901 dated Feb. 27, 2007, 8 pgs.
Office Action Summary from USPTO for U.S. Appl. No. 10/255,901 dated Sep. 6, 2007, 9 pgs.

(56) References Cited

OTHER PUBLICATIONS

Office Action Summary from USPTO for U.S. Appl. No. 10/255,905 dated May 19, 2004, 7 pgs.
Office Action Summary from USPTO for U.S. Appl. No. 10/255,905 dated May 26, 2005, 5 pgs.
Office Action Summary from USPTO for U.S. Appl. No. 10/255,905 dated Feb. 9, 2006, 8 pgs.
Advisory Action Before the Filing of an Appeal Brief from USPTO for U.S. Appl. No. 10/255,905 dated Aug. 11, 2006, 3 pgs.
Office Action Summary from USPTO for U.S. Appl. No. 10/255,905 dated Jan. 30, 2007, 7 pgs.
Notice of Non-Compliant Amendment (37 CFR 1.121) from USPTO for U.S. Appl. No. 10/255,905 dated Jul. 9, 2007, 4 pgs.
Office Action Summary from USPTO for U.S. Appl. No. 10/255,905 dated Oct. 5, 2007, 7 pgs.
Office Action Summary from USPTO for U.S. Appl. No. 09/685,697 dated Jul. 18, 2003, 8 pgs.
Office Action Summary from USPTO for U.S. Appl. No. 09/685,697 dated Feb. 3, 2004, 5 pgs.
Office Action Summary from USPTO for U.S. Appl. No. 09/685,697 dated Jan. 4, 2005, 5 pgs.
Office Action Summary from USPTO for U.S. Appl. No. 09/685,697 dated Oct. 4, 2005, 7 pgs.
Advisory Action Before the Filing of an Appeal Brief from USPTO for U.S. Appl. No. 09/685,697 dated Mar. 13, 2006, 4 pgs.
Office Action Summary from USPTO for U.S. Appl. No. 09/685,697 dated Jun. 26, 2006, 8 pgs.
Office Action Summary from USPTO for U.S. Appl. No. 09/685,697 dated Apr. 10, 2007, 9 pgs.
Office Action Summary from USPTO for U.S. Appl. No. 09/685,697 dated Oct. 9, 2007, 11 pgs.
Office Action Summary from USPTO for U.S. Appl. No. 10/140,635 dated Oct. 3, 2003, 9 pgs.
International Search Report and Written Opinion for International Application No. PCT/US2017/021519 filed Mar. 9, 2017, and mailed from the International Search Authority dated May 22, 2017, 17 pgs.
Non-Final Office Action for U.S. Appl. No. 15/094,424, filed Apr. 8, 2016, and mailed from the USPTO dated May 31, 2017, 68 pgs.
Advisory Action dated Oct. 16, 2017 in U.S. Appl. No. 15/094,424.
Notice of Allowance and Fee(s) Due for U.S. Appl. No. 15/083,810, filed Mar. 29, 2016, and mailed from the USPTO dated Sep. 23, 2016, 14 pgs.
Notice of Allowance and Fee(s) Due for U.S. Appl. No. 14/169,302, filed Jan. 31, 2014, and mailed from the USPTO dated Mar. 4, 2016, 13 pgs.
Final Office Action for U.S. Appl. No. 15/094,424, filed Apr. 8, 2016, and mailed from the USPTO dated Sep. 5, 2017, 35 pgs.
Kothari, R. U. et al., ""Cincinnati Prehospital Stroke Scale: Reproducibility and Validity"", Annals of Emergency Medicine, 33/3, pp. 373-378, https://www.ncbi.nlm.nih.gov/pubmed/10092713, Apr. 30, 1999.
JAMB Innovations, LLC, uBurn, https://web.archive.org/web/20120506154615/https://itunes.apple.com/us/app/uburn/id327057175?mt=8, May 6, 2012.
International Preliminary Report of Patentability for PCT/US2016/064719 filed on Dec. 2, 2016, dated Jul. 5, 2018.
U.S. Appl. No. 16/389,610, Non-Final Office Action, dated Mar. 2, 2020, Mar. 2, 2020.

\* cited by examiner

Specific PAI Target Tool

| Case Exit X-1 | Cord Around Neck/ Body |
| Arrival Interface | Monitor Baby/ Mother |
| Urgent Disconnect | Control Breathing |
| Critical Caller Danger | Seizure PDIs |

( ● ) Adult  ( ○ ) Child  ( ○ ) Infant  ( ○ ) Newborn/ Neonate

PAI Protocol

C. Airway / Arrest / Choking (unconscious) – Adult ≥ 8 Yrs.
D. Choking (Conscious) – Adult / Child / Infant
F. Childbirth - Delivery
L. Sinking Vehicle (1st Party)
M. Childbirth – Delivery (1st Party)
O. Locator Diagnostic
X. Case Exit
YC. Tracheostomy (Stoma) Airway / Arrest / Choking (Unconscious) – Adult ≥ 8 Yrs.
Z. AED Support

PAI Panel

| 1. Phone Type | 15. Identifying Noises |
| 2. Personal Info | 90. Special Communication Methods |
| 3. Vehicle Identification | 91. Signal: Structure Type |
| 4. Location Info | 92. Signal: Street Type |
| 5. Caller Communication Capability | 93. Signal: Street Name |
| 6. General Location | 93a. Signal: Street Info |
| 7. Rural/Wilderness Info | 94. Signal: Apartment Number |
| 8. General Location | 94a. Signal: Apartment Info |
| 9. Personal Residence Info | 95. Signal: Last Name |
| 10. Other Residence Info | 96. Signal: First Name |
| 11. Building Info | 97. Signal: Cell Phone Company |
| 12. Outside Info | 98. Signal: Hears Sirens/Sees Lights |
| 13. Underground Info | 99. Getting Visible/Heard |
| 14. Landmark Info | |

[ ✓ OK ]   [ ✗ Cancel ]

FIG. 6

LOCATOR DIAGNOSTIC SYSTEM FOR EMERGENCY DISPATCH

COPYRIGHT NOTICE

© 2015 Priority Dispatch Corp. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR § 1.71(d).

TECHNICAL FIELD

The present disclosure relates to computer systems and methods for providing emergency protocol interrogation, instruction, and dispatch. More specifically, the disclosure is directed to computer-implemented tools to assist a dispatcher interrogating an emergency caller to identify the emergency caller's location.

BRIEF DESCRIPTION OF THE DRAWINGS

Non-limiting and non-exhaustive embodiments of the disclosure are described, including various embodiments of the disclosure with reference to the figures, in which:

FIG. 6 is a user interface of a locator diagnostic tool for an emergency dispatch system.

DETAILED DESCRIPTION

Figure 1:
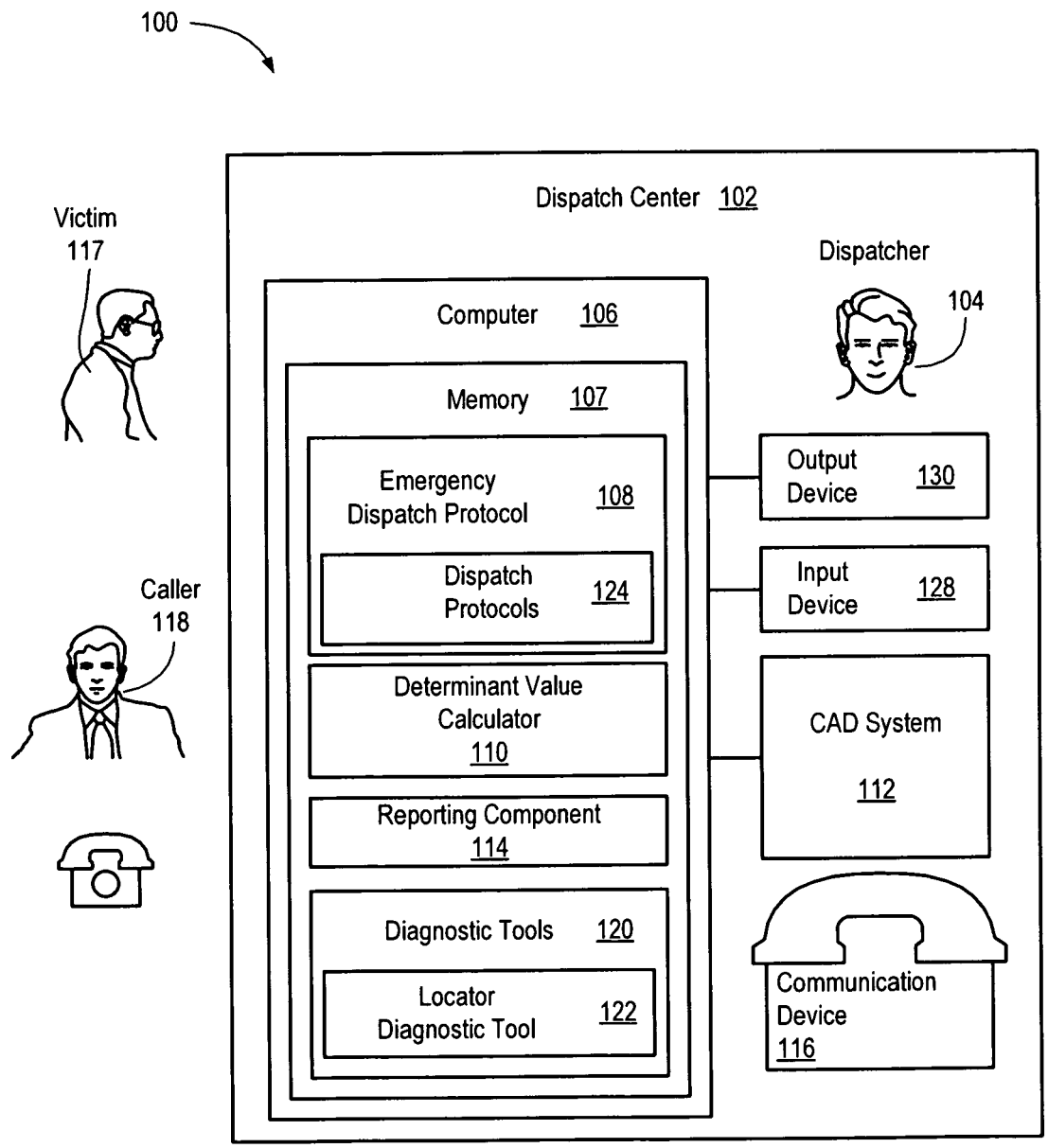
FIG. 1 is a block diagram of an emergency dispatch system, according to one embodiment.

Emergency calls to emergency dispatch centers often require an in-person response from appropriately trained persons (e.g., emergency responders). In many cases, the location of an incident may be reported by the caller and/or determined from the telephone on which the call was made. Sometimes, the caller may not know the location of the incident, and/or the location cannot be determined from the telephone on which the call was made. Emergency responders, such as law enforcement, fire responders, and emergency medical technicians (EMTs), will likely be unable to travel to and address the incident until the location has been determined.

The caller may be unable to identify the incident location for a variety of reasons. The caller may be lost, kidnapped, trapped, or otherwise transported to a location with which the caller is not familiar. Alternatively, or in addition, the caller may have suffered a stroke, be mentally ill, be intoxicated, be suffering from temporary mental defect, and/or the like. The caller also may not know what information will be most useful to the dispatcher in identifying the incident location. Further, the stress of an emergency situation may prevent the caller from thinking of easy and/or straightforward ways of identifying the incident location. As a result, the caller may be unable to inform the dispatcher of the incident location without assistance from the dispatcher.

Other factors may further complicate identifying the location. For example, the caller may be unable to speak due to injury or a nearby threat. Alternatively, the person needing assistance (e.g., patient or victim) may not be with the caller. These complicating factors may make it even more difficult for the caller to inform the dispatcher of the incident location without receiving skilled guidance and interrogation from the dispatcher.

Exigent circumstances may make determination of the incident location critical and place emergency dispatchers in a critical role. Emergency dispatchers may be the first and/or only persons to interface with the caller during an emergency call. In their role of receiving emergency calls, emergency dispatchers are in a unique position and may potentially contribute to more positive outcomes by quickly determining the incident location and/or efficiently gathering information that will allow emergency responders to ascertain the incident location, for example, when searching in the field. Unfortunately, often emergency dispatchers are inexperienced and unskilled, largely due to a high turnover rate among emergency dispatchers.

An automated emergency dispatch system, potentially implemented on a computer, can aid even an unskilled and inexperienced dispatcher in prioritizing emergency calls that are received and in processing the calls to generate an appropriate emergency dispatch response. Regardless of the experience or skill level of the dispatcher, the automated emergency dispatch system can enable a consistent and predictable emergency dispatch response, despite the diverse aspects of emergency situations that may be reported from one call to the next.

Although existing automated emergency dispatch systems can enable receiving and processing of widely divergent aspects of emergency situations, these systems may not be well suited for processing particular types of unique situations. More particularly, an automated emergency dispatch system may not be well suited to providing the guidance and interrogation needed to determine the incident location and/or efficiently gather information about the location. Special diagnostic procedures may be required to provide the required guidance and properly record information provided by the caller. A diagnostic tool providing additional interrogation and instructions and/or alternative emergency dispatch procedures or protocols may facilitate more positive results when the incident location is not readily known by the caller.

Existing automated emergency dispatch systems are not equipped to assist or enable a dispatcher to process an emergency call involving a caller who does not know the incident location. A dispatcher unfamiliar with helping a caller to identify an incident location and/or untrained in handling the same may not be able to compensate for the shortcomings of an automated emergency dispatch system. Inexperienced and/or unskilled dispatchers are generally unable to initiate or assist a proper response from emergency responders, or to provide effective advice to callers. Even highly skilled and experienced dispatchers may have little skill or experience with handling incidents for which the caller does not know the location, simply because such incidents may be relatively rare compared to other types of incidents that are reported. Accordingly, the present disclosure provides a method and system for processing of emergency calls involving callers who do not know the incident location, in a quick, efficient, and predictable manner.

The embodiments of the disclosure will be best understood by reference to the drawings, wherein like parts are designated by like numerals throughout. It will be readily understood that the components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments of the disclosure. In addition, the steps of a method do not necessarily need to be executed in any specific order, or even sequentially, nor need the steps be executed only once, unless otherwise specified.

In some cases, well-known features, structures or operations are not shown or described in detail. Furthermore, the described features, structures, or operations may be combined in any suitable manner in one or more embodiments. It will also be readily understood that the components of the embodiments as generally described and illustrated in the figures herein could be arranged and designed in a wide variety of different configurations.

Several aspects of the embodiments described will be illustrated as software modules or components. As used herein, a software module or component may include any type of computer instruction or computer-executable code located within a memory device and/or computer-readable storage medium. A software module may, for instance, comprise one or more physical or logical blocks of computer instructions, which may be organized as a routine, program, object, component, data structure, etc. that performs one or more tasks or implements particular abstract data types.

In certain embodiments, a particular software module may comprise disparate instructions stored in different locations of a memory storage device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

Suitable software to assist in implementing the invention is readily provided by those of skill in the pertinent art(s) using the teachings presented here and programming languages and tools, such as Java, Pascal, C++, C, database languages, APIs, SDKs, assembly, firmware, microcode, and/or other languages and tools.

An emergency dispatch system as disclosed herein may be computer-implemented in whole or in part on a digital computer. The digital computer includes a processor performing the required computations. The computer further includes a memory in electronic communication with the processor to store a computer operating system. Computer operating systems may include, but are not limited to, MS-DOS, Windows, Linux, Unix, AIX, CLIX, QNX, OS/2, and Apple. Alternatively, it is expected that future embodiments will be adapted to execute on other future operating systems. The memory may also store application programs including a Computer Aided Dispatch (CAD) program, an automated emergency dispatch protocol, and a user interface program. The memory may also include data storage. The computer may further include an output device, such as a display unit, for viewing the displayed instructions and inquiries, and a user input device for inputting response data.

FIG. 1 illustrates an emergency dispatch system 100, according to one embodiment. At a dispatch center 102, a dispatcher 104 may operate a computer 106 or other computing device. The computer 106 may include a memory 107 to store protocols, modules, tools, data, etc. The computer 106 may be configured to follow an emergency dispatch protocol 108 to enable the dispatcher 104 to rapidly and consistently address an emergency incident, such as a crime, a medical problem, or an incident otherwise requiring a response from emergency professionals, as reported by a caller 118. An emergency call requesting emergency professionals may report an incident that may involve a victim and/or patient 117. As can be appreciated, in some circumstances and/or incidents, the caller 118 is the victim and/or patient 117. In other instances the caller 118 may be a second party (e.g., a person with the victim and/or patient 117), third party (e.g., a person not in the immediate vicinity of the victim and/or patient 117), fourth party (e.g., a reporting or referral agency), or suspect (or perpetrator). The emergency dispatch protocol 108 may include a logic tree, preprogrammed inquiries or questions, possible responses from a caller 118 to the inquiries, and instructions to the caller 118. The responses may route to subsequent preprogrammed inquiries and/or instructions to the caller 118. The emergency dispatch protocol 108 may be subdivided into a plurality of protocols, such as a case entry protocol to gather basic caller information and a complaint-specific dispatch protocol 124 for guiding the dispatcher 104 in processing emergency calls involving specific situations and/or incidents. The complaint-specific dispatch protocols 124 may similarly include a logic tree, preprogrammed inquiries or questions, possible responses from a caller 118 to the preprogrammed inquiries, and instructions for the caller 118.

The responses of the caller 118 are processed according to predetermined logic of the logic tree of the emergency dispatch protocol 108. The predetermined logic may enable the emergency dispatch system 100 to provide to the dispatcher 104 information concerning the correct emergency dispatch response (e.g., by trained law enforcement officers or agencies, emergency medical technicians (EMTs) and/or other emergency responders). The predetermined logic may also enable the emergency dispatch system 100 to provide to the dispatcher 104 appropriate post-dispatch instructions for relay to the caller 118 before professional help arrives at the scene. The predetermined logic may also enable the emergency dispatch system 100 to aid the dispatcher 104 in determining an appropriate priority of the emergency call, including but not limited to a priority of the emergency call relative to other emergency calls and a level of emergency response to provide for the reported incident or situation.

Although the emergency dispatch system 100 is disclosed and described in some sections herein with reference to an emergency police dispatch system, a person of ordinary skill can appreciate that other emergency dispatch systems and protocols are contemplated, including but not limited to emergency medical dispatch systems and protocols and emergency fire dispatch systems and protocols. Exemplary embodiments of emergency dispatch systems and protocols are disclosed in U.S. Pat. Nos. 5,857,966; 5,989,187; 6,004, 266; 6,010,451; 6,053,864; 6,076,065; 6,078,894; 6,106, 459; 6,607,481; 7,106,835; 7,428,301; 7,436,937; 7,645, 234; 8,066,638; 8,103,523; 8,294,570; 8,335,298; 8,355, 483; 8,396,191; and 8,417,533, which are hereby incorporated herein by reference.

The computer 106 operates a determinant value calculator 110 to calculate a determinant value from the responses of the caller 118 to protocol questions. The determinant value may be selected from a group of pre-established determinant values, such that the emergency responders are familiar with the determinant values and understand the meaning of each and what would be a corresponding emergency response. For example, the determinant values may range, for example, from E-1 for generally very serious emergencies to Ω-2 for generally less serious emergencies. The determinant value may provide a categorization code of the type and level of the incident.

In one embodiment of the present disclosure, the determinant value is a combination of a determinant level (Alpha A, Bravo B, Charlie C, Delta D, Echo E and Omega Ω) and a numeric value. Generally, Ω-2 is the least serious while E-1 is the most serious call. Depending on the determinant level, the appropriate emergency response is dispatched as indicated by the response protocol. For example, an Alpha-A call will typically be responded to by a next available emergency response unit using the safest arrival method reasonably possible. A Delta-D call will typically be responded to by any or all available emergency response units proceeding under the most urgent method possible. Echo-E calls typically involve likely immediate life-threatening situations and will be responded to in the most urgent manner available. Bravo-B and Charlie-C calls are intermediate calls that are typically responded to in business-like, orderly manner according to specific department protocol. An Omega-Ω call is generally not specifically responded to, but rather is referred to another person or agency. For the purposes of this disclosure, Echo-E is generally abbreviated as E; Delta-D is generally abbreviated as D; Charlie-C is generally abbreviated as C; Bravo-B is generally abbreviated as B; Alpha-A is generally abbreviated as A; and Omega-Ω is generally abbreviated as Ω. Generally, the lower determinant levels (e.g., numbers) within a determinant classification are more urgent than higher numbers. For example, an emergency dispatch call with a determinant value of D-1 is generally more critical and requires a more urgent response than a call with a determinant value of D-2. However, in some instances, the numeric determinant levels within a determinant value may serve only to identify the type, rather than criticality of the call. Also, if more than one determinant value can be assigned to a particular call, the more critical or higher determinant value is assigned. That is, the call is assigned a criticality determinant value based on the fact or aspect that would lead to the most urgent response. For example, if the call concerns a burglary that occurred over 30 minutes before, but where the suspect remains on the scene or nearby and the caller 118 indicates that he or she is still in danger and feels his or her life is in imminent danger, then the determinant value assigned would be E-1 (due to the imminent danger) rather than D-2 (suspect on scene or nearby) or B-1 (incident occurred over 30 minutes before).

Many calls to emergency dispatchers are not true emergencies, so it is important to prioritize the calls in several ways. First, calls that are true emergencies should be dispatched first. Second, if an agency has units with different capabilities, the emergencies involving more severe problems can be sent units that are more skilled and advanced (e.g., a S.W.A.T. team or bomb squad). And finally, if lights and siren are not needed, they should not be used, thereby increasing the safety of all those on the road and in the emergency response vehicles. The computer 106 presents the determinant value to generate an appropriate emergency dispatch response and/or establish the priority of the emergency call. The response may include dispatching professional law enforcement officers, EMTs, or other emergency responders to the scene of the emergency. The protocols used shall have passed through a rigorous review by a panel of experienced law enforcement agents and EMS public safety experts.

The determinant value may be provided to a Computer Aided Dispatch (CAD) system 112, which is a tool that a dispatcher 104 may use to track and allocate emergency response resources for processing emergency calls. The CAD system 112 may manage dispatcher tools for processing emergency calls, including but not limited to the emergency dispatch protocol 108, communication resources (e.g., radio system, alpha pager), mapping tools (e.g., global positioning system (GPS) technology, geographic information systems (GIS)), and vehicle location systems (e.g., automatic vehicle location (AVL)). The CAD system 112 may operate in whole or in part on a separate computer in communication with the computer 106. In another embodiment, the CAD system 112 operates on the computer 106. The primary information used by the CAD system 112 is location information of the incident and units, unit availability, and the type of incident. The CAD system 112 may use third party solutions, such as E-911, vehicle location transponders, and mobile data terminals (MDTs) for automating the location and availability tasks. The CAD system may also use an emergency dispatch protocol 108 to facilitate structured call taking for incident interrogation, as previously described.

Although many emergency calls are not true emergencies, all situations can benefit from expert evaluation and pertinent instruction. Prior to the arrival of professional help on-scene, the emergency dispatch protocol 108 may provide the dispatcher 104 with instructions for the caller 118 that are appropriate to the type of call, whether the call relates to a complaint of vandalism or to a homicide. These instructions may help expedite the work of law enforcement officers, EMTs, and/or other emergency responders.

The computer 106 may include a reporting component 114 to statistically measure the performance of individual staff and overall performance of the dispatch center 102. To record information received during a call, the dispatcher 104 may be required to open a new case. Once the call is complete, the dispatcher 104 may close the case, and a case summary may be saved. The case summary may be retrieved later for review and/or analysis. The reporting component 114 may determine statistics from the case summaries and/or while the cases are open. The statistics may include compliance rates, call processing statistics, and peer measurements.

The computer 106 may further comprise an input device 128, such as a keyboard, mouse, touch screen, laser pointer, or other input device, and also an output device 130, such as a display monitor. The input device 128 receives input from a user (generally a dispatcher 104) and provides the input to the emergency dispatch system 100. The input may be provided to the computer 106, the emergency dispatch protocol 108, a diagnostic tool 120, and/or the CAD system 112. An output device 130 receives output from the emergency dispatch system 100 and displays or otherwise provides the output to the user. In another embodiment, the input device 128 and output device 130 are provided by the CAD system 112.

The dispatch center 102 includes a communication device 116 (e.g., telephone equipment) to answer emergency calls. In some embodiments, the communication device 116 may be coupled to the computer 106 to enable the computer 106 to send and/or receive text messages and/or to identify dual-tone multi-frequency (DTMF) signals received at the communication device 116. A call into the dispatch center 102 from a caller 118 may initiate creation of an emergency call incident. The dispatcher 104 identifies the call as requiring an emergency dispatch, and the emergency dispatch protocol 108 is accessed. The protocol 108, including the complaint-specific dispatch protocols 124, may provide questions and/or instructions that are expertly drafted to assist a novice caller 118 in reporting aspects of the incident, and/or assessing a situation of a victim and/or patient 117. The protocol 108 may also provide expertly drafted instructions to assist a victim and/or patient 117 prior to the arrival of trained law enforcement and/or emergency responders. The instructions may be vocally relayed by the dispatcher 104 to the caller 118 over the communication device 116.

Some protocol inquiries or questions may be readily answerable by the caller 118, whereas others may be more difficult to answer. Certain diagnostic inquiries may be difficult for the untrained caller 118 to determine or may be difficult to answer under the stress of an emergency situation. Accordingly, in addition to instructions, the emergency dispatch system 100 may provide one or more computer-implemented diagnostic tools 120. The diagnostic tools 120 may greatly improve information collection and intervention for emergency response situations and aid in saving lives.

A diagnostic tool 120 may aid the dispatcher 104 and/or the caller 118 (via instructions from the dispatcher 104) in assessing a situation of a victim and/or patient 117. A diagnostic tool 120 may also be an interventional tool, providing instructions that direct a caller 118 to intervene, or take action, to aid a victim and/or patient 117, or otherwise change the circumstances or conditions of an emergency situation. For sake of clarity, diagnostic tools and interventional tools are both referred to herein generally as diagnostic tools. Accordingly, a diagnostic tool 120, as referred to herein, may provide diagnostic instructions, interventional instructions, or both diagnostic and interventional instructions. Whether a diagnostic tool 120 provides merely diagnostic instructions, merely interventional instructions, or both diagnostic and interventional instructions, the diagnostic tool 120 provides consistent and reliable instruction, information gathering, and/or timing for a particular emergency situation.

The diagnostic tools 120 are computer-implemented software modules that enable a dispatcher 104 to provide consistent, expert advice to assist a caller 118 with regards to a particular aspect of an emergency situation. In highly stressful conditions, the diagnostic tools 120 provide a necessary resource to reading critical signs. The diagnostic tools 120 may be stored in the memory 107 of the computer 106 and initiated and executed as required. The diagnostic tools 120 may be embodied as computer-executable software applications and associated data.

The emergency dispatch protocol 108, including the case entry protocol and/or the complaint-specific dispatch protocols 124, also may call on one or more diagnostic tools 120 to assist with an inquiry and may route to the appropriate diagnostic tool 120 when needed. When directed according to the protocol, the emergency dispatch protocol 108 may automatically, i.e., without dispatcher intervention, initiate the appropriate diagnostic tool 120. This may occur when the emergency dispatch protocol 108 arrives at a diagnosis or assessment step in the logic tree. The emergency dispatch system 100 may also allow the dispatcher 104 the option to call upon a diagnostic tool 120 as desired. Icons and/or buttons may be displayed in a tool bar or other convenient location on a user interface to allow the dispatcher 104 to initiate a corresponding diagnostic tool 120. In another embodiment, the emergency dispatch protocol 108 may simply prompt the dispatcher 104 to launch the appropriate diagnostic tool 120 when needed.

The diagnostic tool 120 discussed herein comprises a locator diagnostic tool 122. The locator diagnostic tool 122 may be configured to guide the dispatcher 104 in gathering information that can be used to identify the incident location and/or aid emergency responders in the field in finding the incident. The locator diagnostic tool 122 may be launched automatically or manually if the incident location is unknown. The locator diagnostic tool 122 may traverse a logical tree to determine which questions to present to the dispatcher 104 for submission to the caller 118. The dispatcher 104 may input information indicative of caller responses to the questions. The dispatcher-entered input may be used by the diagnostic tool 120 to decide which path of the diagnostic tree to traverse and to determine the next question to ask.

For example, the locator diagnostic tool 122 may take different paths and/or provide additional instruction based on whether the caller 118 is able to talk freely. Similarly, divergent sets of questions may be asked depending on whether the caller 118 is at the incident location or the caller 118 is a third party caller. Different paths may be taken for urban and/or suburban areas versus rural and/or wilderness areas and/or based on whether the incident location is inside, outside, or underground. If the caller 118 indicates a non-specific location, such as a car, a building, a mine, or the like, the locator diagnostic tool 122 may present questions about that non-specific location and/or launch a description diagnostic.

Various methods may be used to identify the caller's location from the responses to the questions presented by the locator diagnostic tool 122. In some situations, the caller 118 may be able to take an action that will send the incident location to the dispatcher 104 and/or another emergency service, such as activating a vehicle locator, activating an emergency pendant, calling from another phone, or the like. The stress of the situation, injury/illness of the caller 118, and/or the like may prevent the caller 118 from taking straightforward actions to determine the incident location. Accordingly, the caller 118 may be given instructions that allow the caller 118 to determine the incident location, such as by looking at a piece of mail, finding another person, looking at a building address, using a global positioning system (GPS) device, or the like. In other situations, a coordinated search may be needed. The locator diagnostic tool 122 may facilitate searching for the incident, such as by storing the responses to all questions, requesting the direction from which sirens or talking are coming, instructing the caller 118 to make noise, and/or the like.

Figure 2:
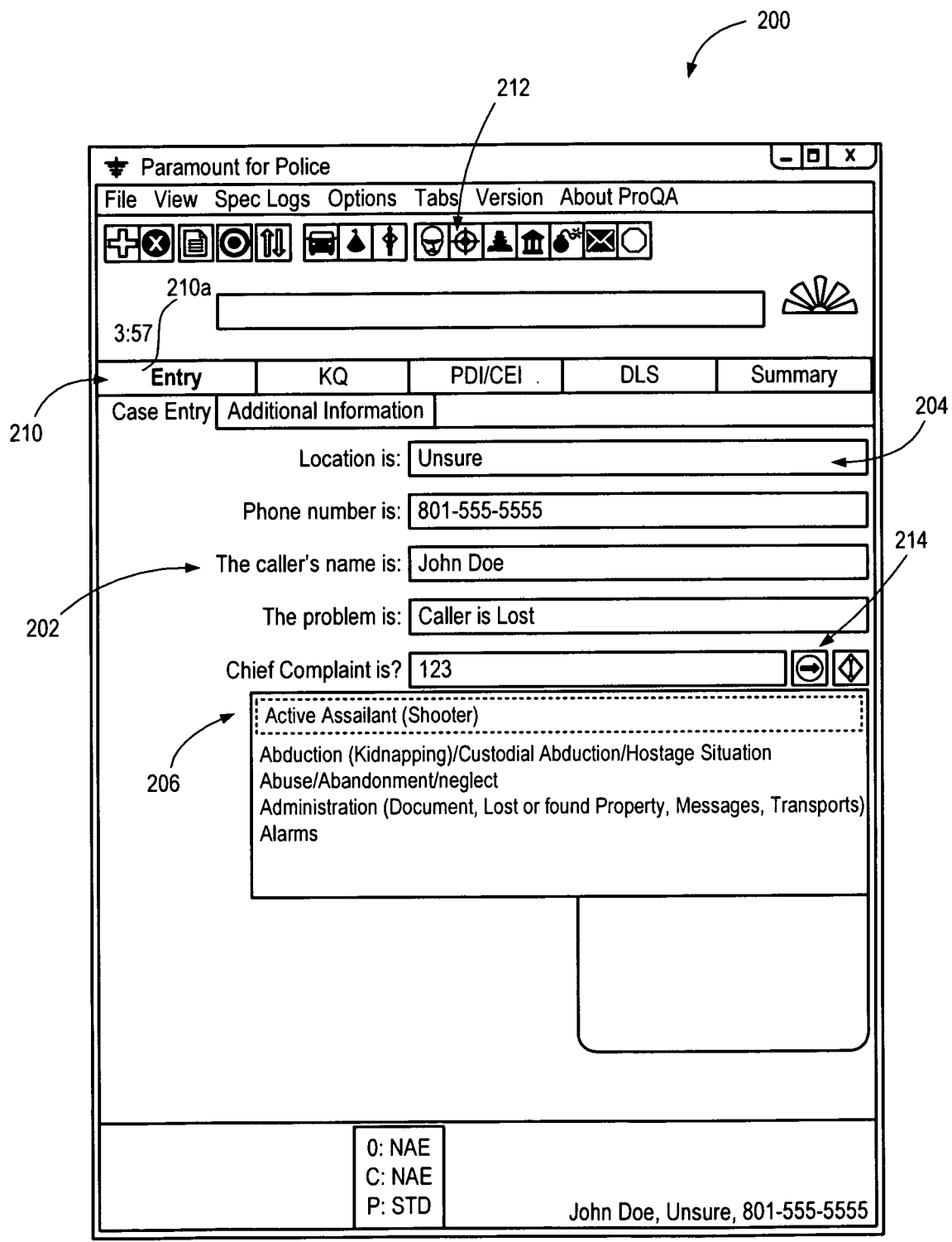
FIG. 2 is a user interface of an emergency dispatch system, according to one embodiment.

FIG. 2 is a user interface 200 of an emergency police dispatch system, according to one embodiment. Although an interface 200 of an emergency police dispatch system is included in the illustrated embodiment, the disclosure may also be applied to emergency fire dispatch systems, emergency medical dispatch systems, and/or the like. The emergency police dispatch system user interface 200 allows a dispatcher 104 to interface with the emergency police dispatch protocol 108. The illustrated user interface 200 is shown traversing a case entry protocol portion of the emergency police dispatch protocol 108. The emergency police dispatch protocol 108 may present inquiries 202 (or questions) via the emergency police dispatch system user interface 200. The inquiries 202 are provided for the dispatcher 104 to relay to the caller 118 to gather information regarding the reported incident or emergency. The dispatcher 104 and/or the emergency police dispatch system may gather the information in the form of caller responses to the inquiries 202. The dispatcher 104 may input the responses of the caller 118 to the inquiries into response fields 204 provided by the user interface 200. The response fields 204 may include, for example, any of a number of appropriate input field types, including but not limited to text fields, text boxes, menus, drop-down menus, drop-down selection boxes, lists, buttons, check boxes, radio buttons, and/or hybrid fields. For example, a text field for identifying the problem may allow for freeform input but also provide a list of suggestions (e.g., echo situations 206) to the dispatcher 104 that can be inserted into the text field by clicking and/or double-clicking an entry in the list. The response fields 204 may correspond to information indicative of one or more responses of the caller 118 to the inquiries 202. In some embodiments, the inquiries 202 may change from an interrogative form to an assertional form after a response has been entered and/or when a cursor is not in the corresponding response field 204.

The caller responses are relayed from the caller 118 to the dispatcher 104, typically over the telephone. Information from the caller responses may be input into the system by the dispatcher 104 and may be used by the emergency police dispatch protocol 108 to determine subsequent inquiries 202 and instructions to present to the dispatcher 104. The caller response information may indicate the caller's observations of the incident and/or current situation. The emergency police dispatch system may use the caller response information to generate an emergency police dispatch response by properly trained law enforcement officers. The information gathered from the caller responses may be used by the determinant value calculator 110 to calculate a determinant value that can be communicated to the emergency responders. Additional details relating to emergency police dispatch protocols and user interfaces to interact with the same can be found in the earlier referenced U.S. patents.

The user interface 200 may further comprise tabs 210 to aid in organizing and/or compartmentalizing various aspects of processing a call. The tabs 210 may include a tab 210a for presenting a case entry protocol portion of an emergency police dispatch protocol 108 (e.g., "Entry" tab). Other tabs may include a tab for presenting a complaint-specific dispatch protocol portion of the emergency police dispatch protocol 108 (e.g., a "KQ" tab or Key Questions tab), a tab for presenting post-dispatch instructions and/or critical EMD information (e.g., a "PDI/CEI" tab), a tab for dispatching life support (e.g., a "DLS" tab), and a tab summarizing the call and/or processing of the call (e.g., "Summary" tab).

The caller 118 may indicate that the incident location is unknown and/or that the caller 118 is unsure of the incident location. In response, the user interface 200 may automatically launch the locator diagnostic tool 122. Alternatively, or in addition, the user interface 200 may provide a locator diagnostic button 212 that can be used to launch the locator diagnostic tool 122. In some embodiments, the user interface 200 may complete the case entry protocol portion of the emergency police dispatch protocol 108 before automatically launching the locator diagnostic tool 122. Alternatively, or in addition, the locator diagnostic tool 122 may interrupt the case entry protocol portion of the emergency police dispatch protocol 108, and the case entry protocol portion of the emergency police dispatch protocol 108 may continue where it left off once the locator diagnostic tool 122 has been completed.

The user interface 200 may provide an input component 214 for the dispatcher 104 to indicate when the portion of the emergency police dispatch protocol 108 presented by the tab 210a has been completed. The input component 214 may be a navigation button, as illustrated in FIG. 2, to enable a dispatcher 104 to provide input that indicates to the user interface 200 that the dispatcher 104 is ready to proceed to a next phase of the emergency police dispatch protocol 108. The dispatcher 104 may also be able to double-click on a chief complaint; use arrow keys, tabs, and/or the Enter or Return key to indicate a chief complaint; or the like to jump to the portion of the dispatch protocol for that complaint. Additional details relating to dispatch protocols for specific complaints and user interfaces to interact with the same can be found in the earlier referenced U.S. patents.

Figure 3:
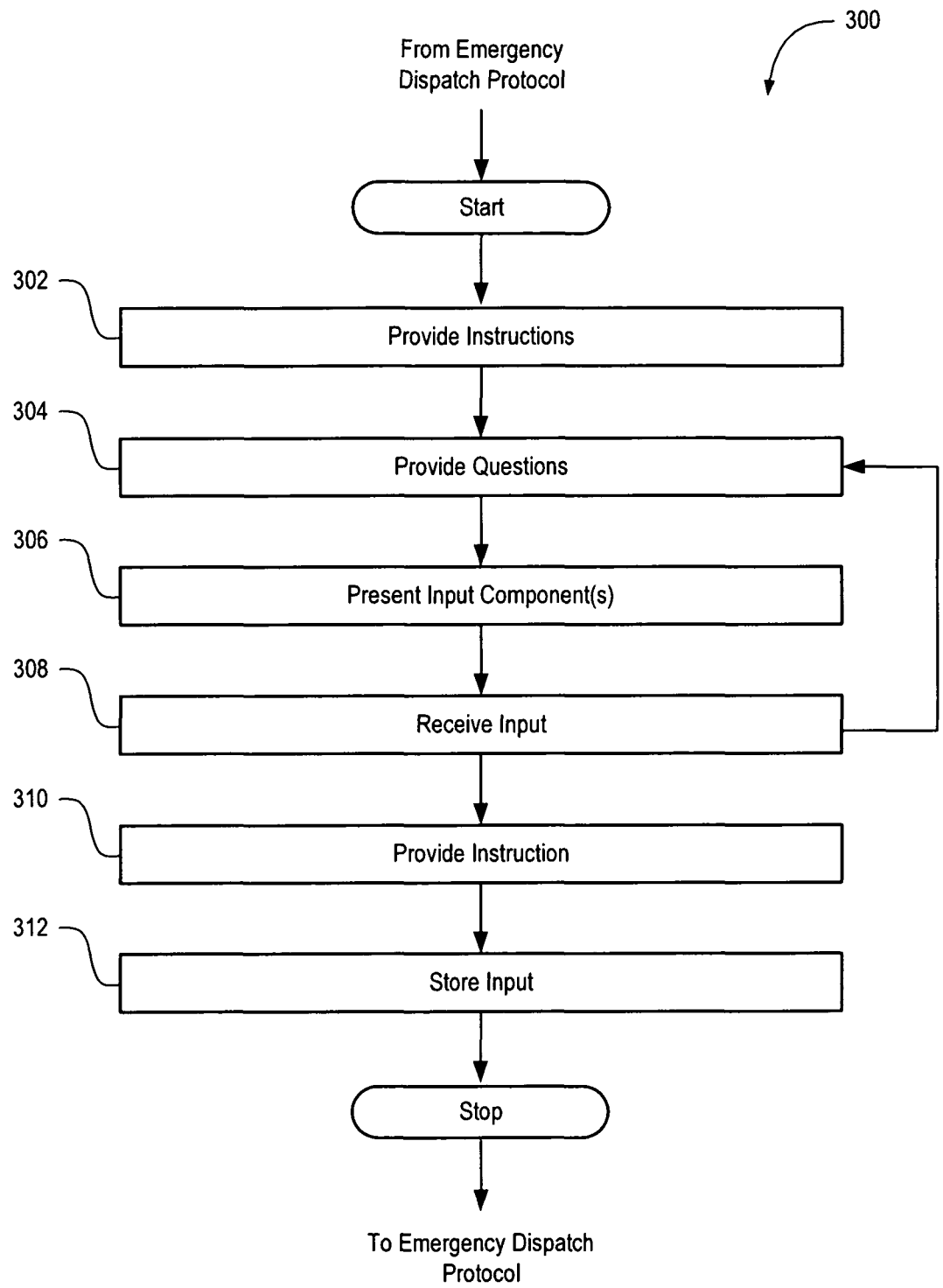
FIG. 3 is a high-level flow diagram of a protocol of a locator diagnostic tool for an emergency dispatch system, according to one embodiment.

FIG. 3 is a high-level flow diagram of a protocol 300 of a locator diagnostic tool 122, according to one embodiment. The locator diagnostic tool 122 may be initiated (e.g., launched) from within the emergency dispatch protocol 108. The emergency dispatch protocol 108 may automatically launch the tool 122 based on input received by the emergency dispatch protocol 108 indicating that the incident location is unknown. The locator diagnostic tool 122 may also be launched manually, as desired, by the dispatcher 104. Upon launching, the locator diagnostic tool 122 may present a user interface.

The protocol 300 may provide 302 an instruction to the dispatcher 104, such as an instruction indicating that emergency responders will be dispatched, but more information is needed to determine the incident location. The protocol 300 may also provide 304 a question for the dispatcher 104 to direct to the caller 118 to provide information concerning the incident location. The protocol 300 may present 306 one or more input components to enable the dispatcher 104 to provide the protocol 300 with input corresponding to a caller response to the question. The protocol 300 may receive 308 the dispatcher-entered input through the one or more input components. The protocol 300 may provide 304 additional questions, present 306 one or more input components for entering input corresponding to responses to those additional questions, and receive 308 the dispatcher-entered input of caller responses to the additional questions. The protocol 300 may determine which additional questions to provide based on the dispatcher-entered input responsive to previously provided questions.

The protocol 300 may provide 310 instructions to the dispatcher 104 to relay to the caller 118 to determine the location, and/or instructions for the caller 118 once all questions have been answered. For example, the caller 118 may be instructed to activate a device that will indicate the caller's location, the instructions may direct the caller 118 to find information indicative of the caller's location, and/or the instructions may let the caller 118 know that the information provided is being saved. Once the instructions have been provided 310 and/or if there are no additional questions, the protocol 300 may store 312 the dispatcher-entered input for each question asked. When the logic flow of the protocol 300 ends, control may be transferred back to the emergency dispatch protocol 108.

Figure 4A:
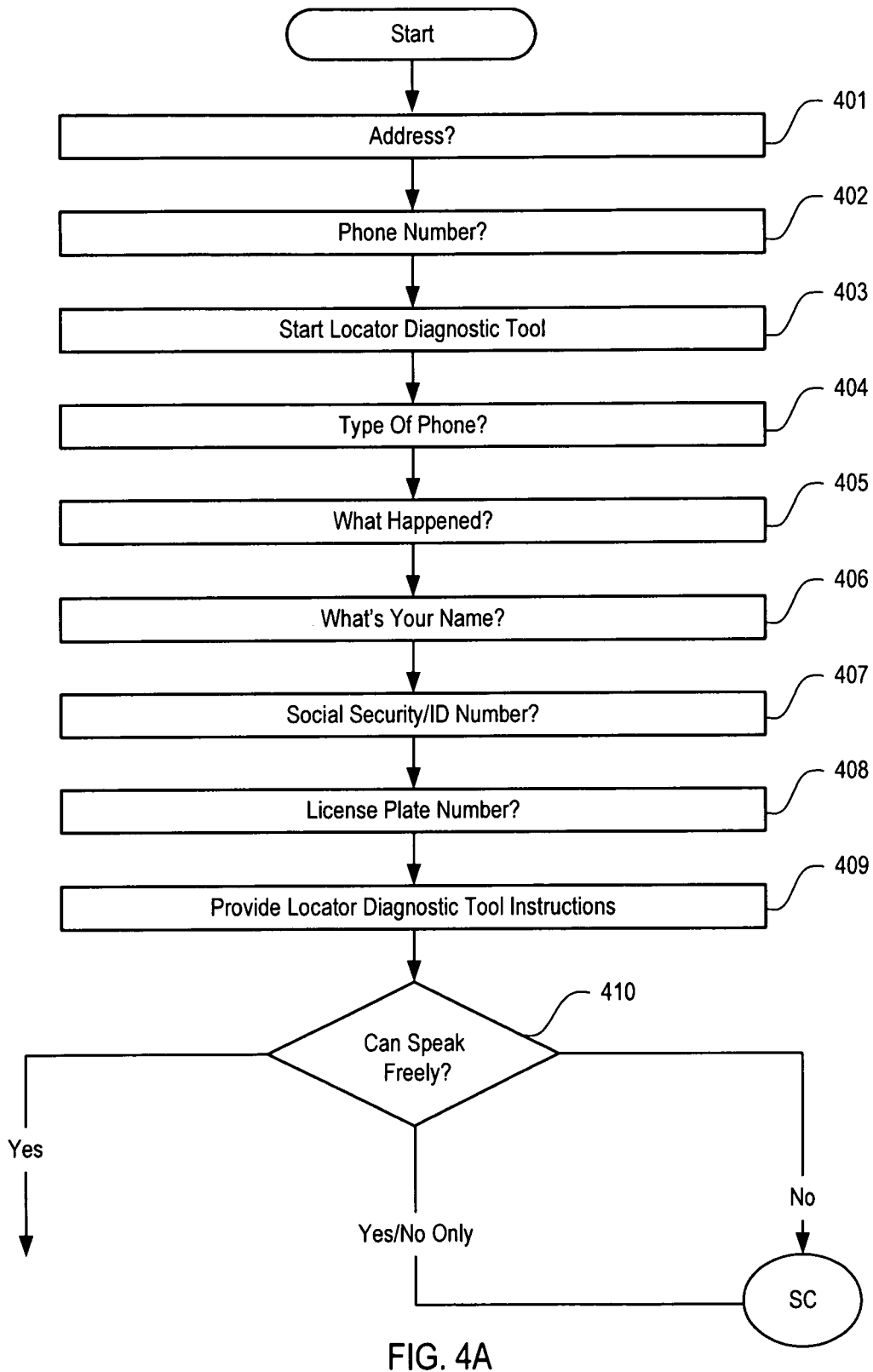
FIGS. 4A-Q are a detailed flow diagram of a method of a locator diagnostic tool for an emergency dispatch system, according to one embodiment.
Figure 4B:
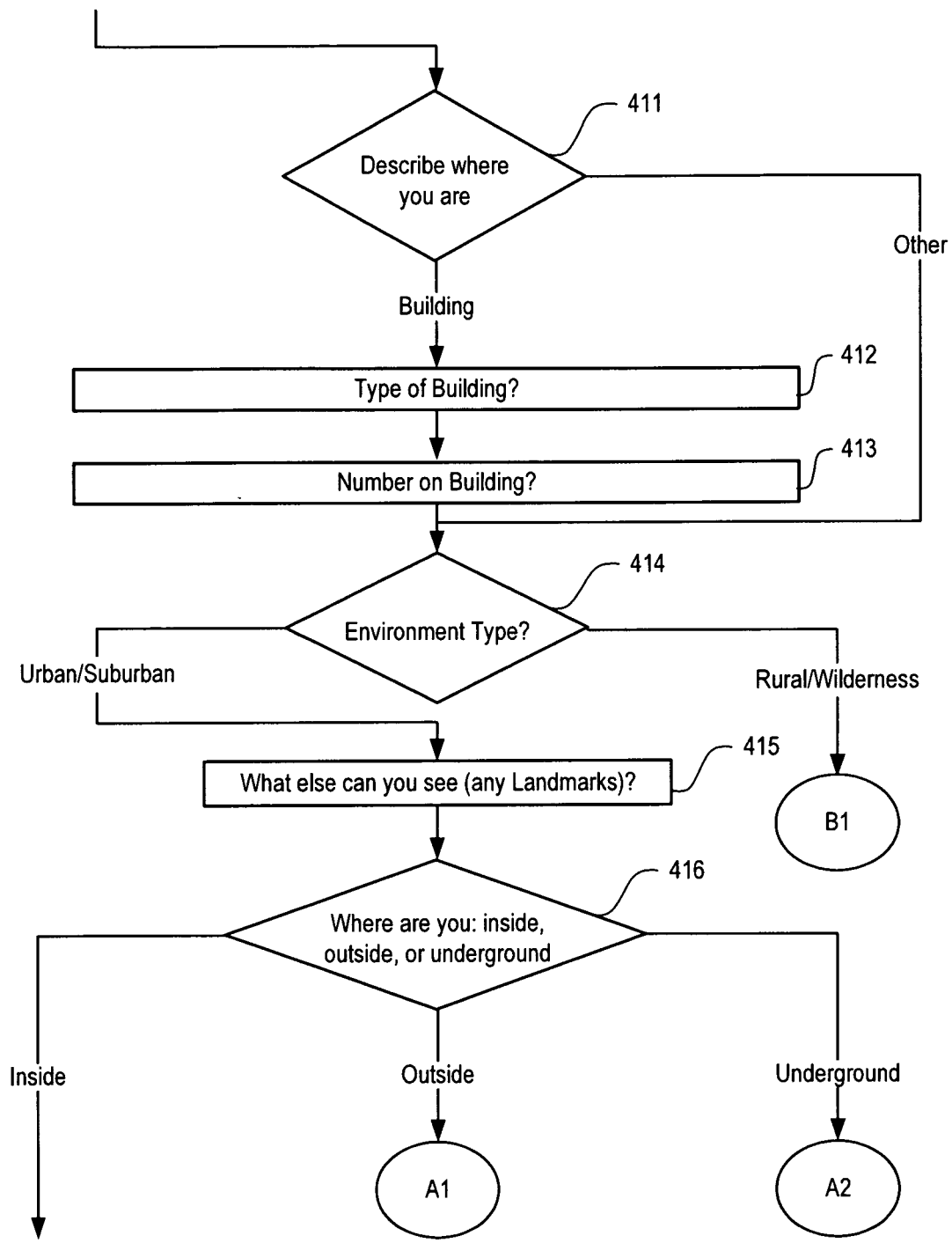
Figure 4C:
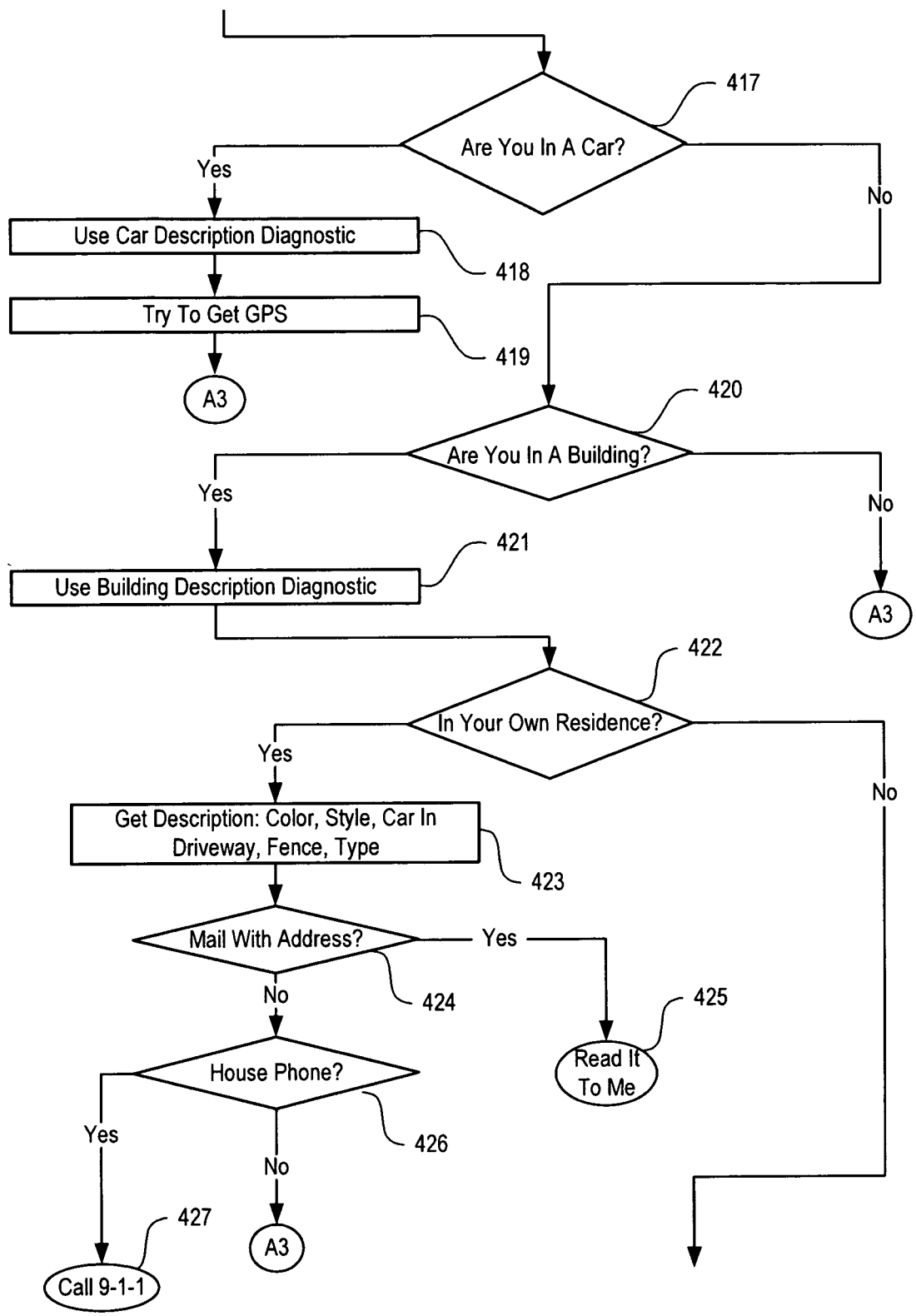
Figure 4D:
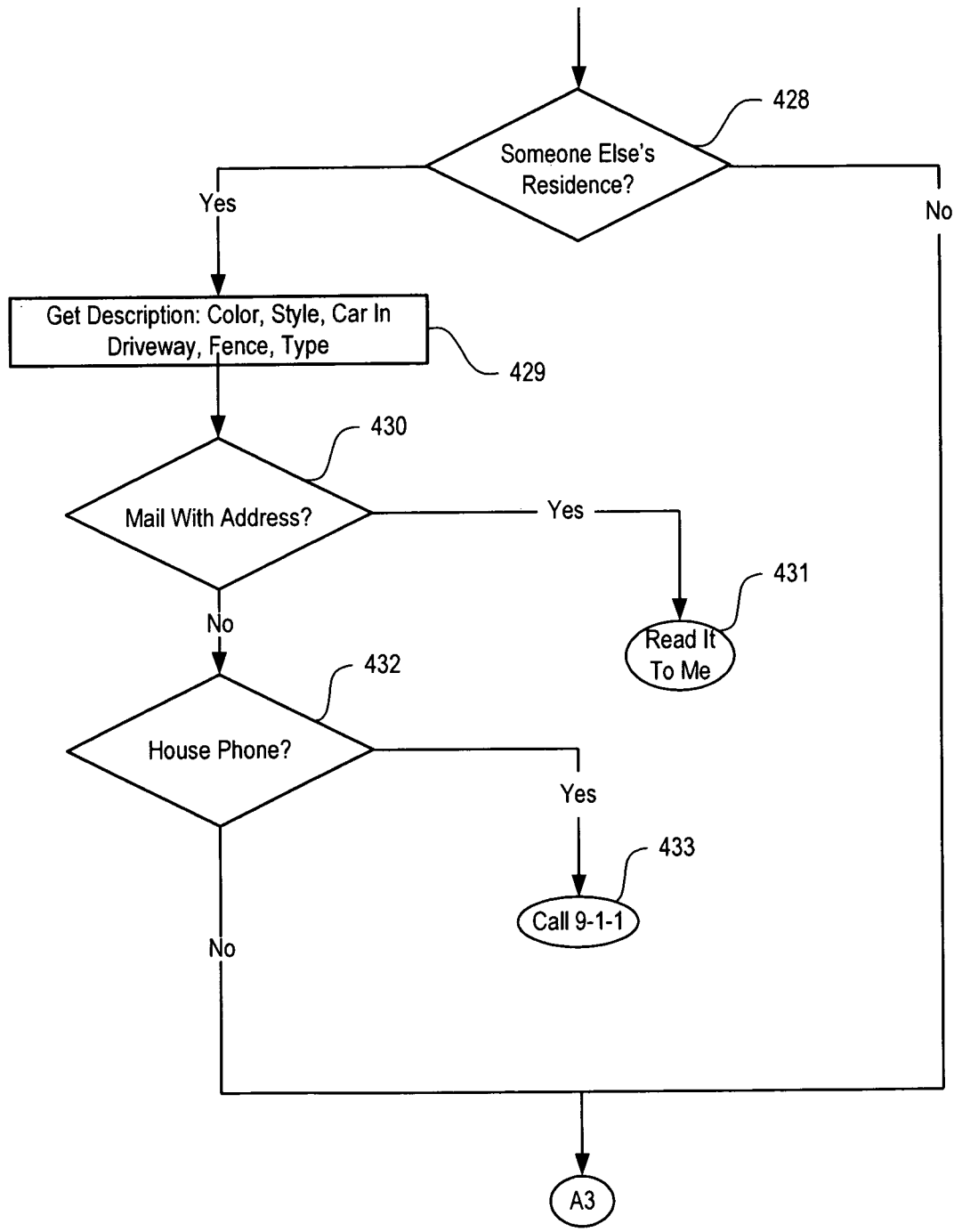
Figure 4E:
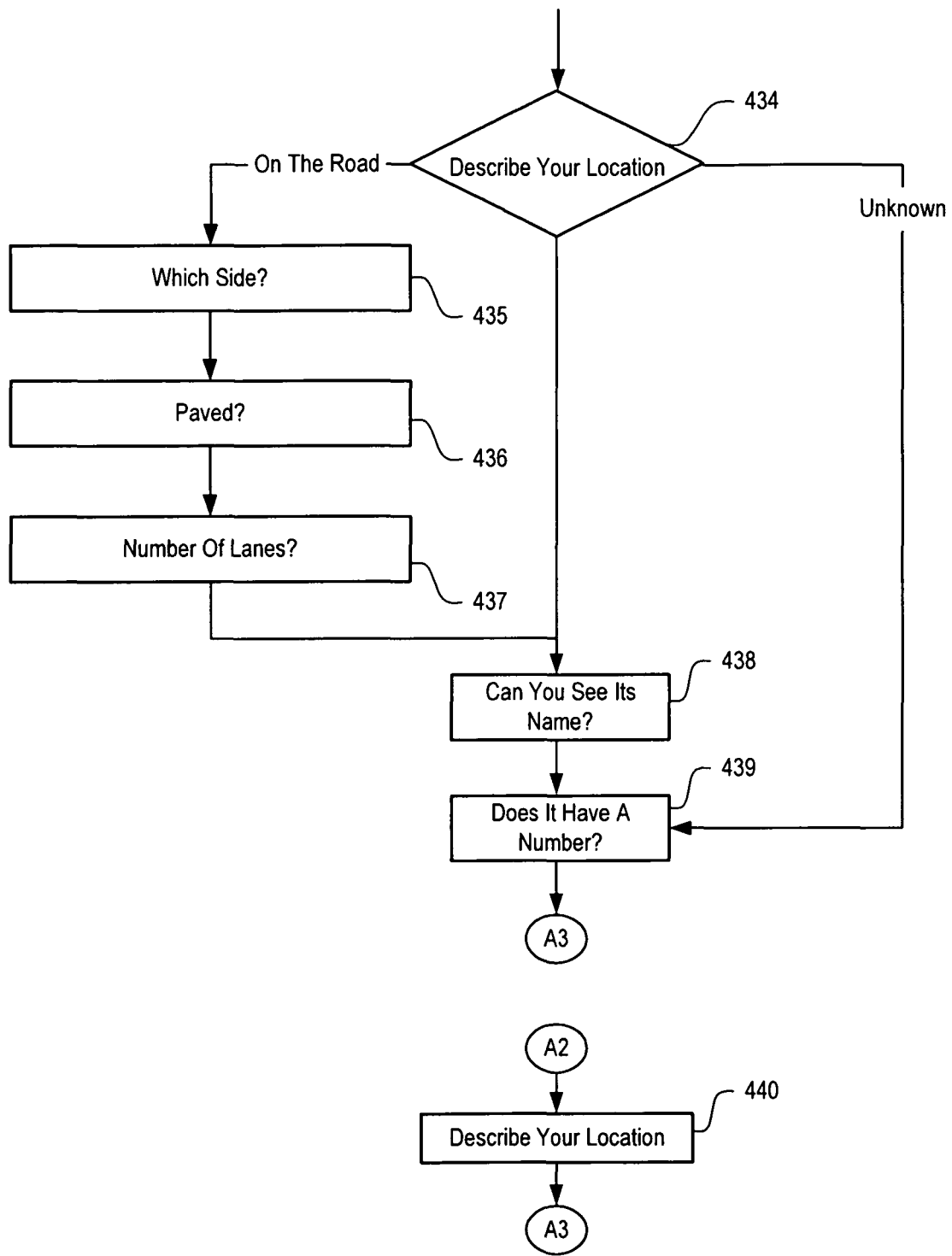
Figure 4F:
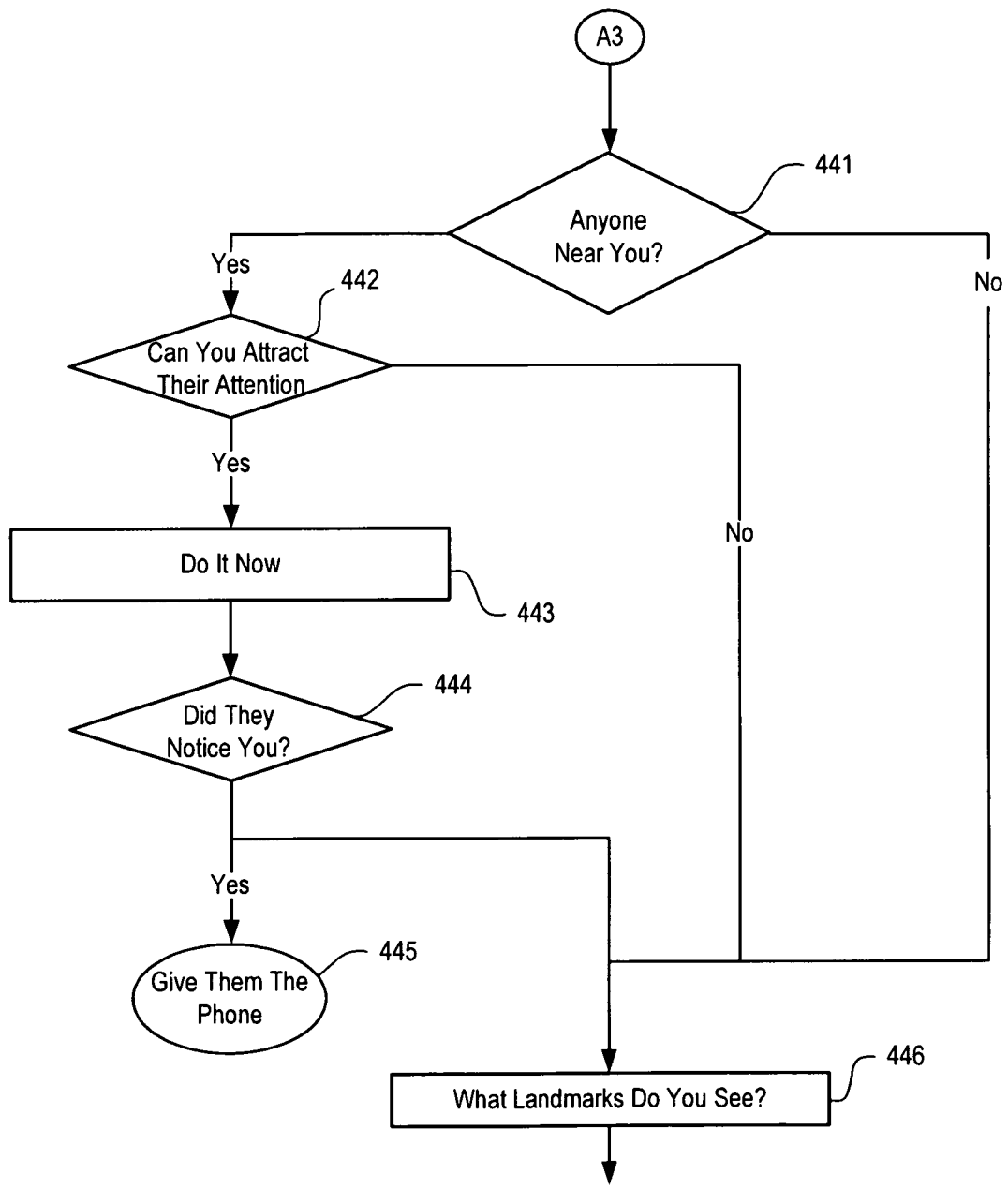
Figure 4G:
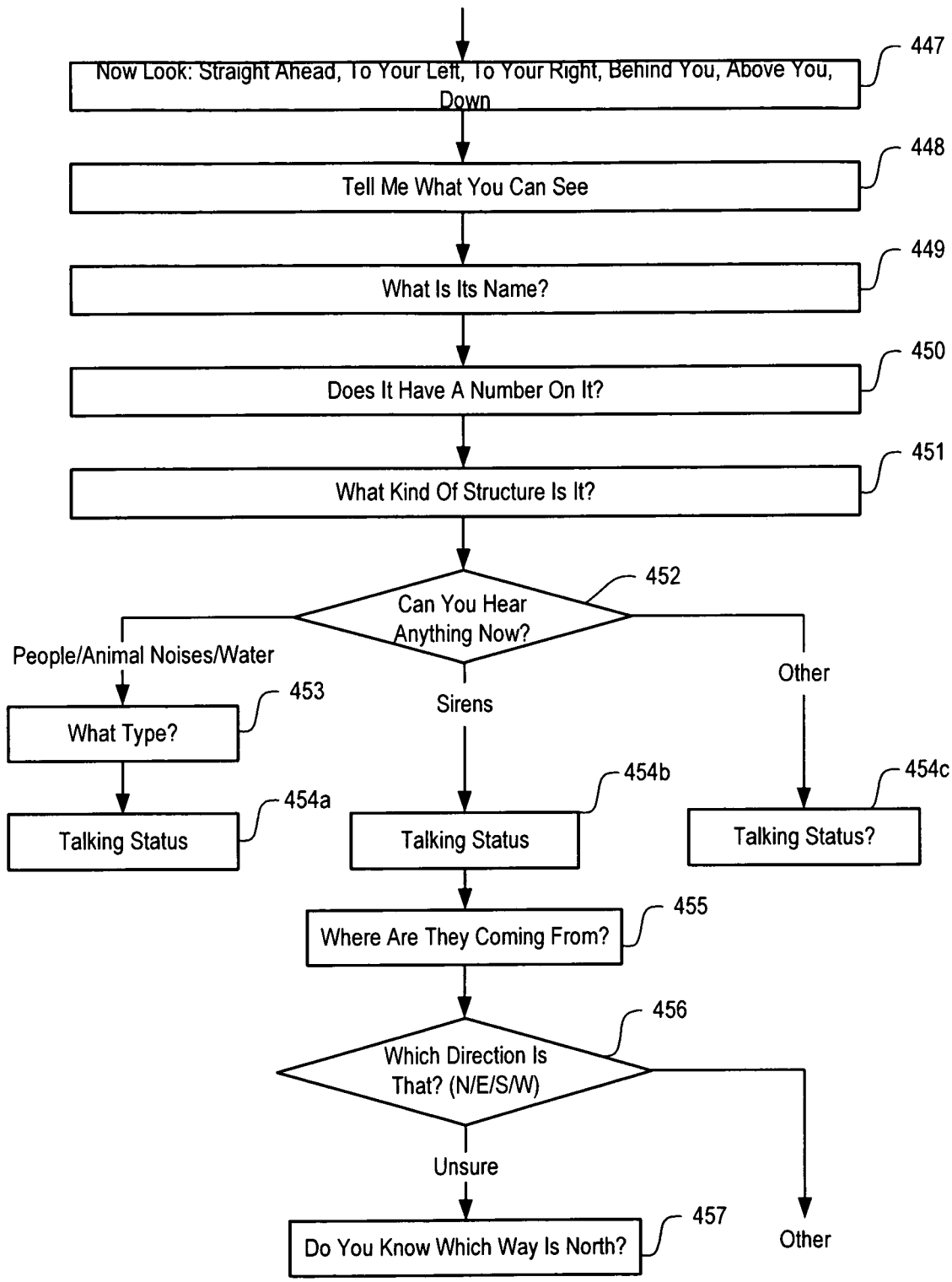
Figure 4H:
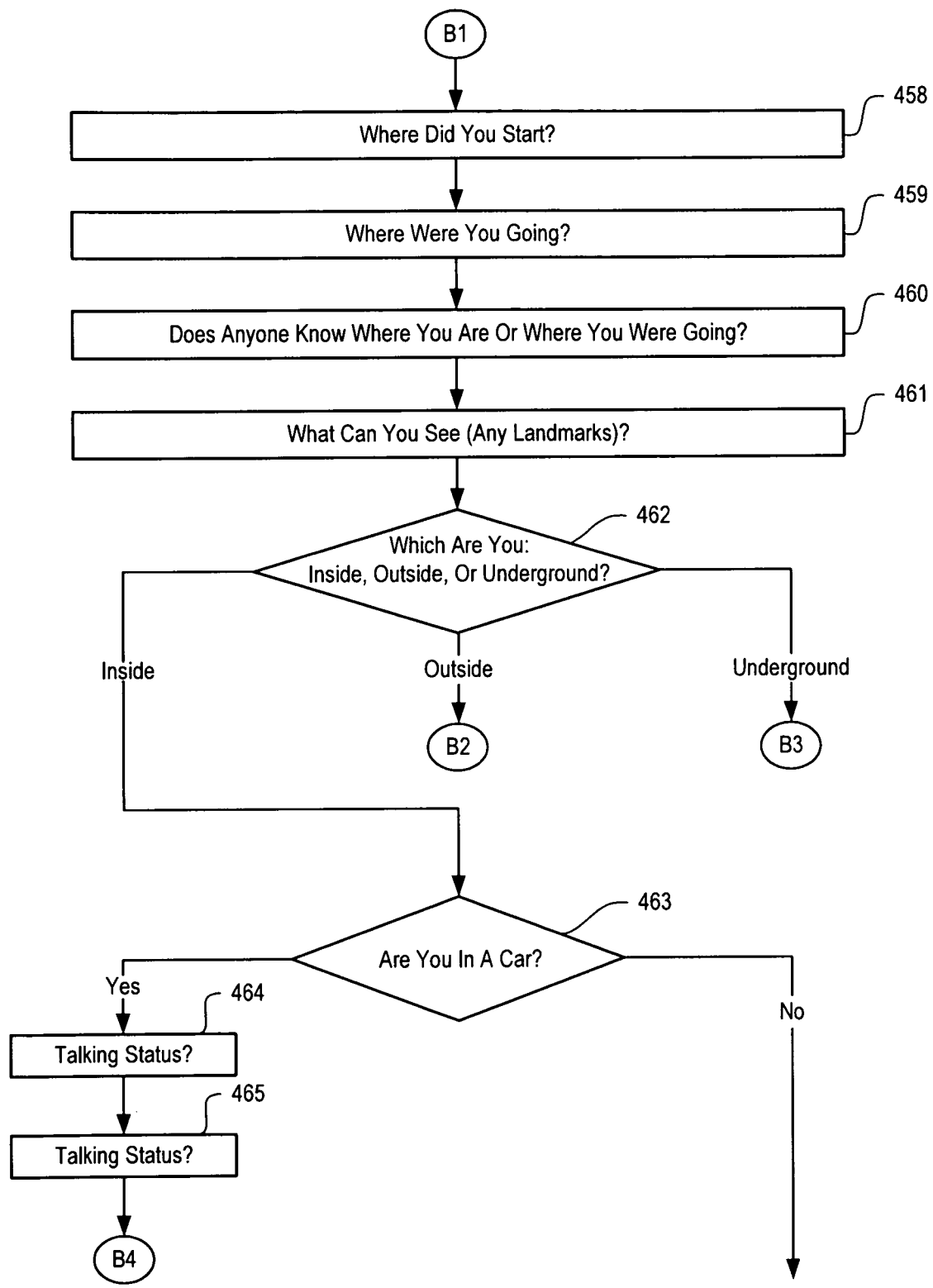
Figure 4I:
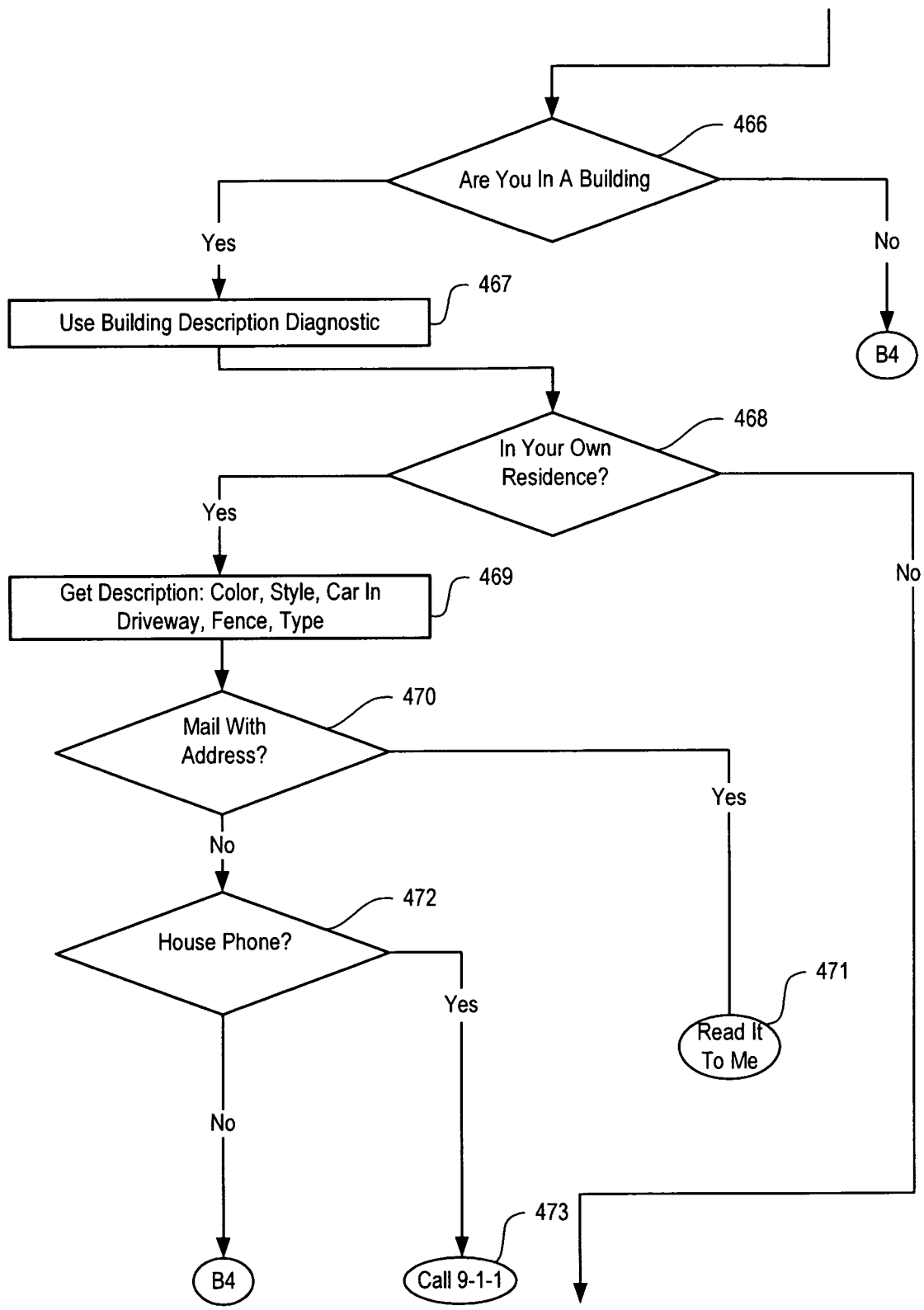
Figure 4J:
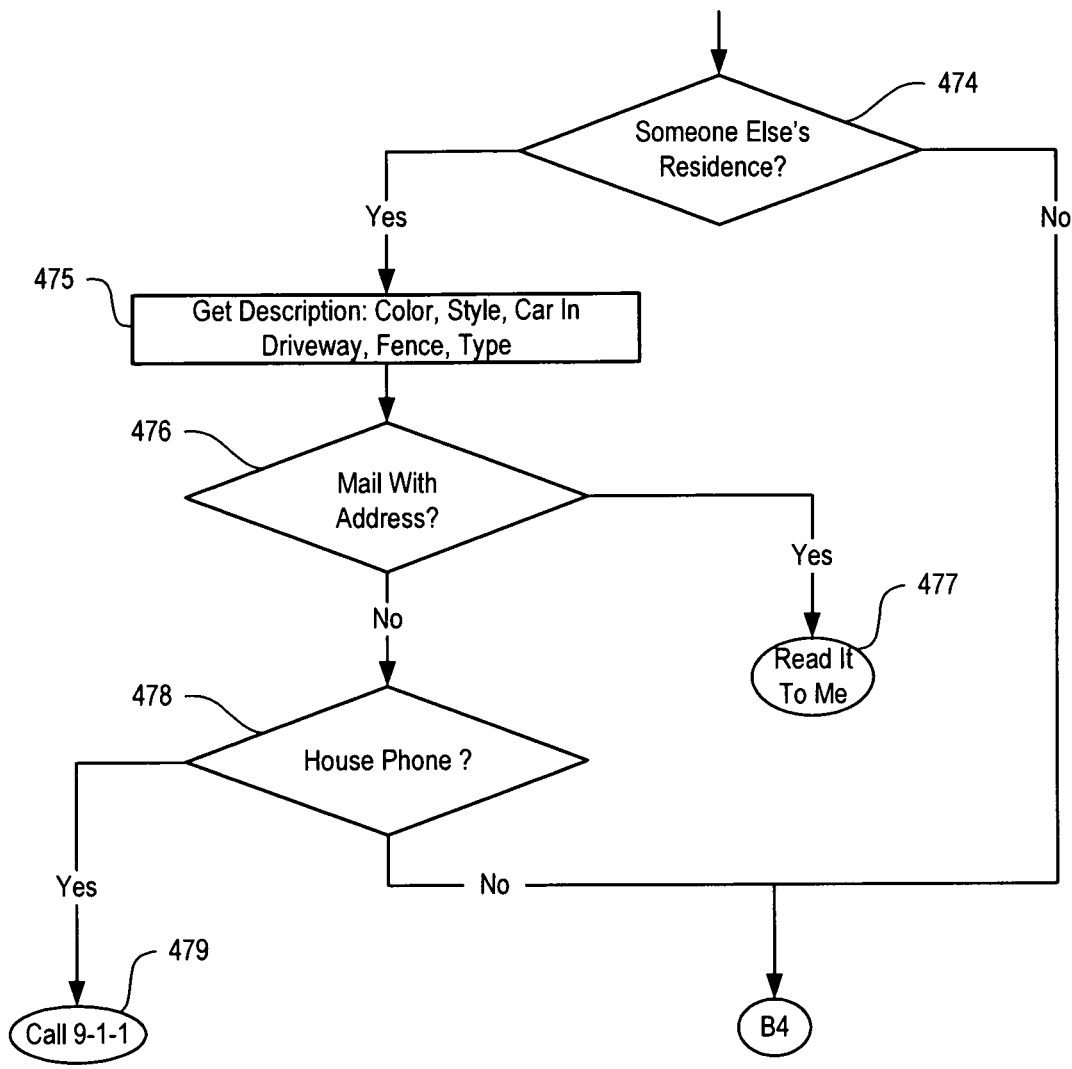
Figure 4K:
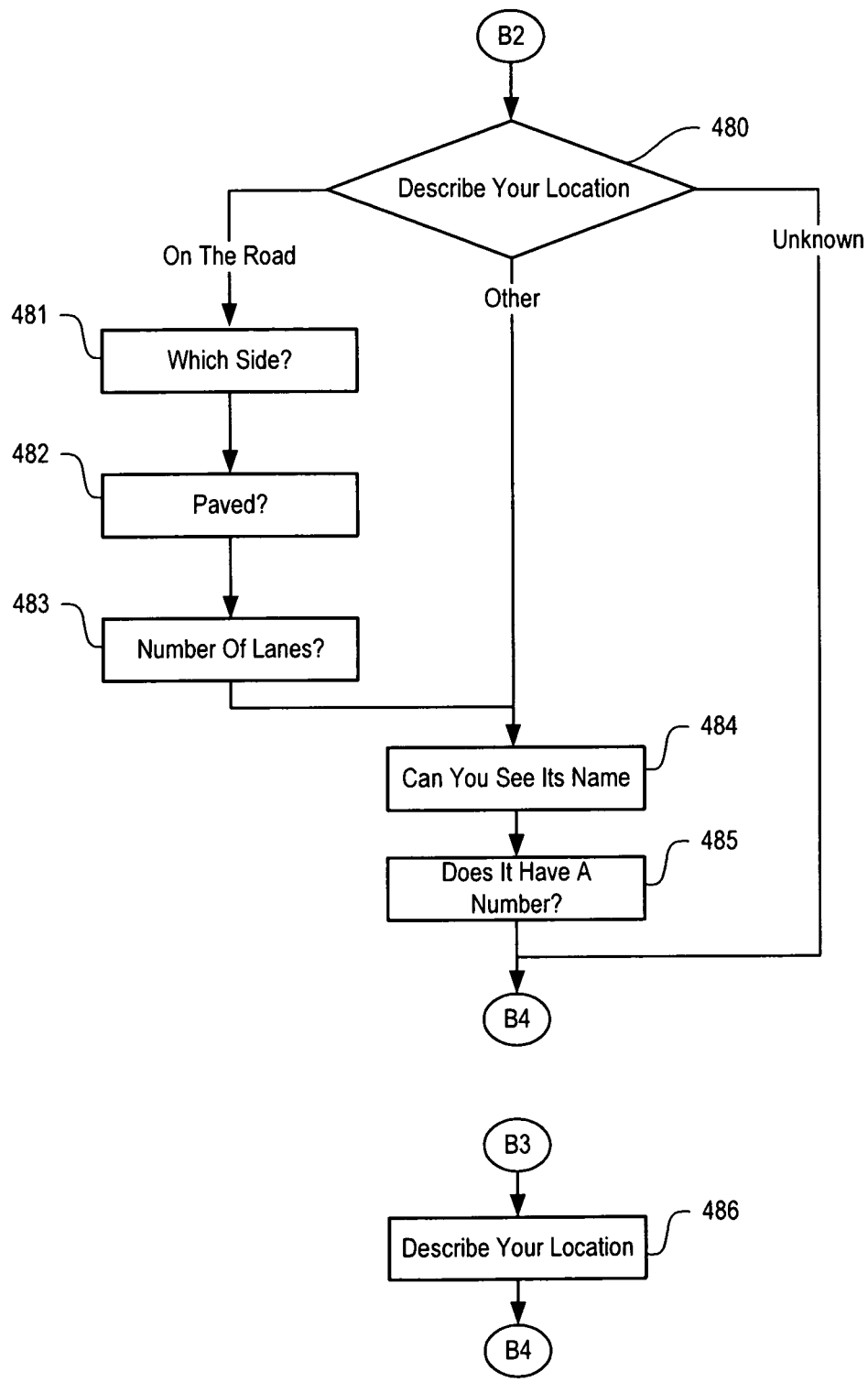
Figure 4L:
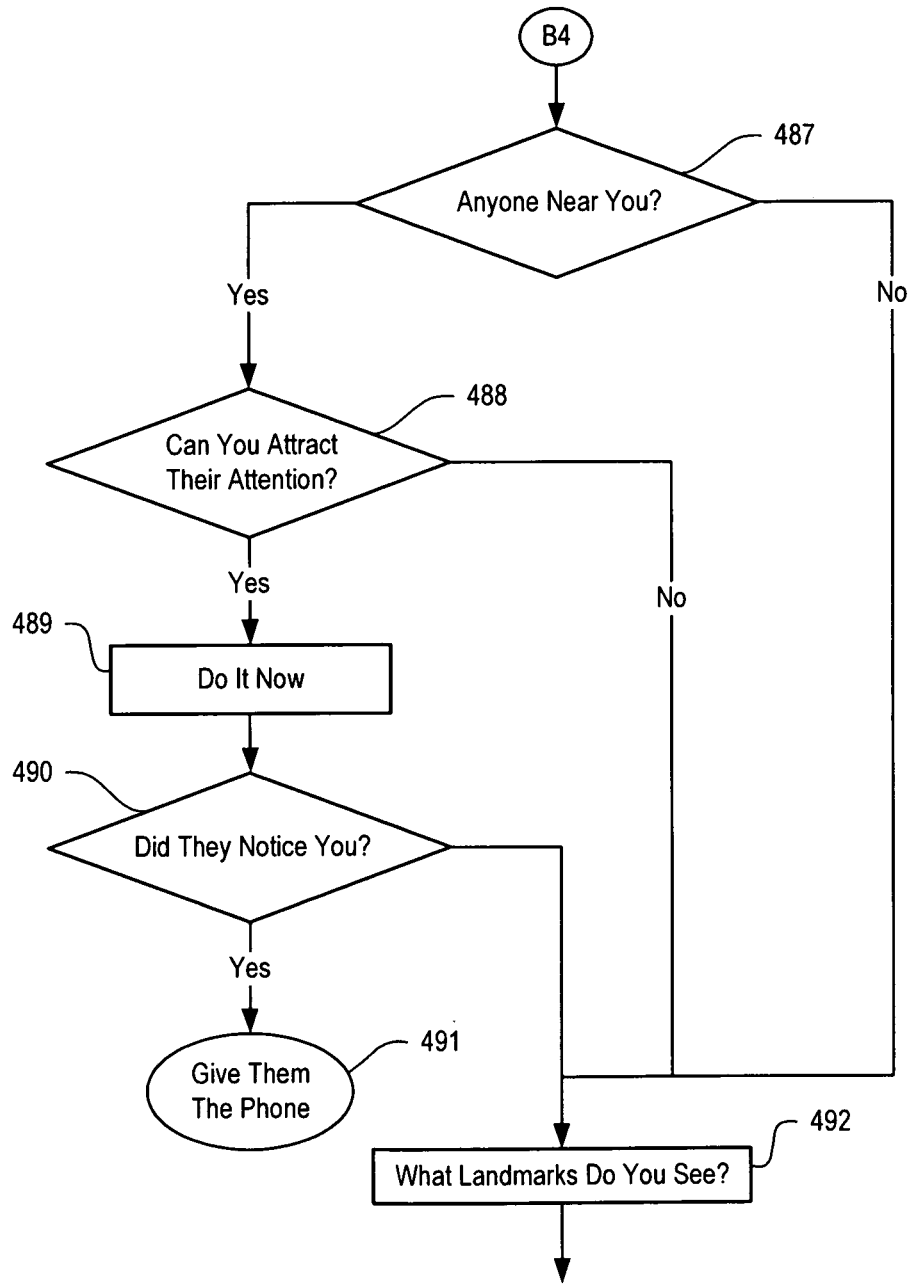
Figure 4M:
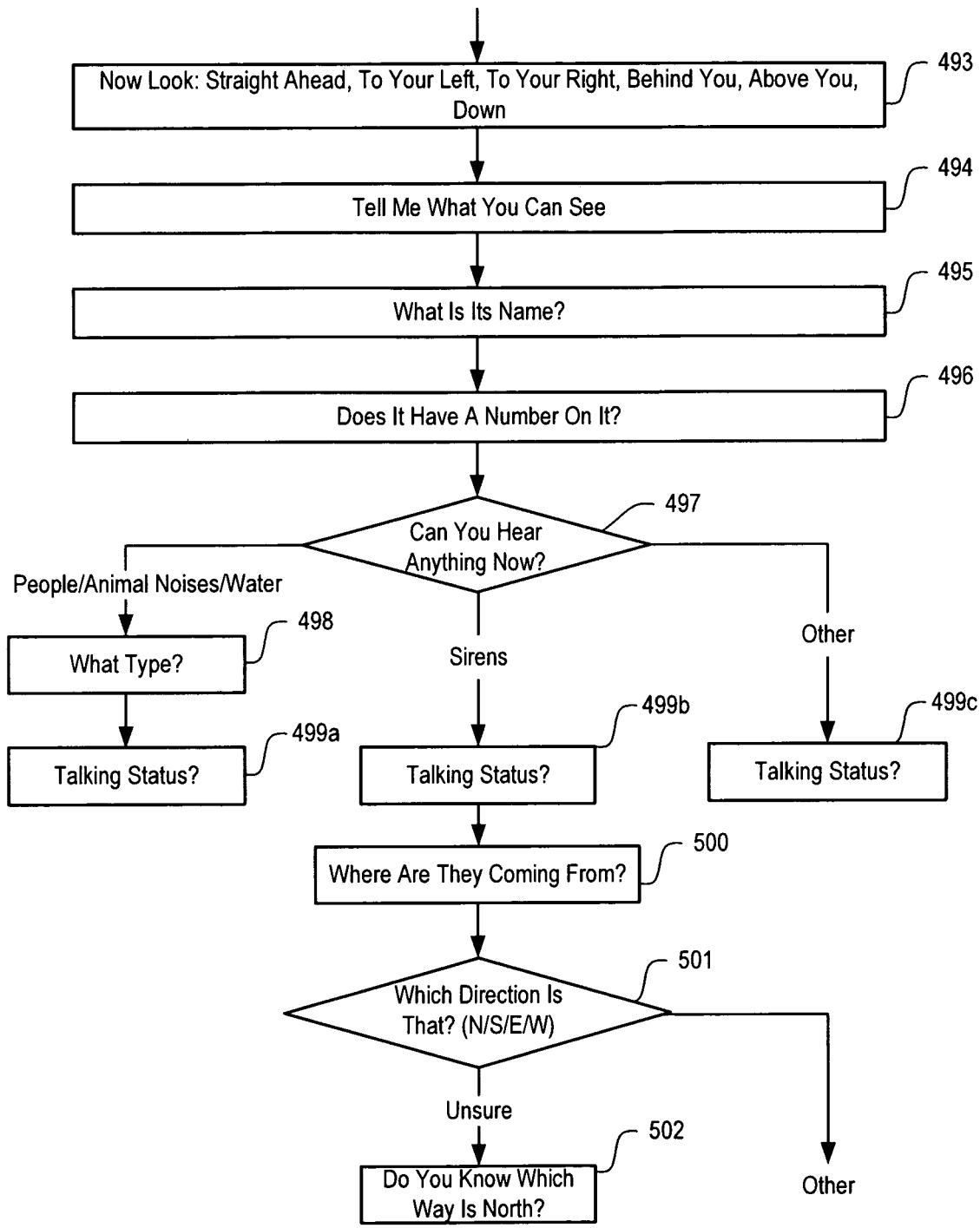
Figure 4N:
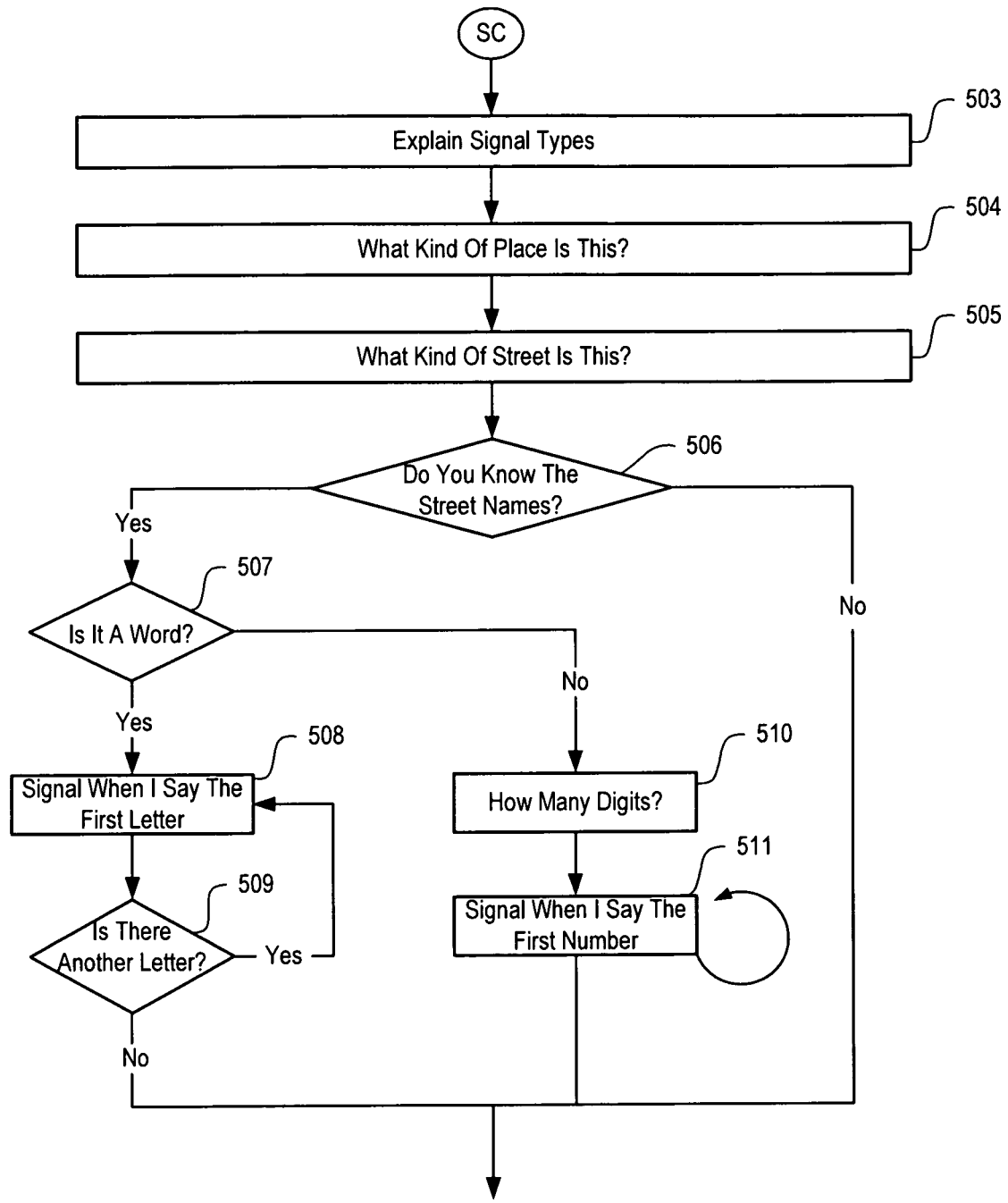
Figure 40:
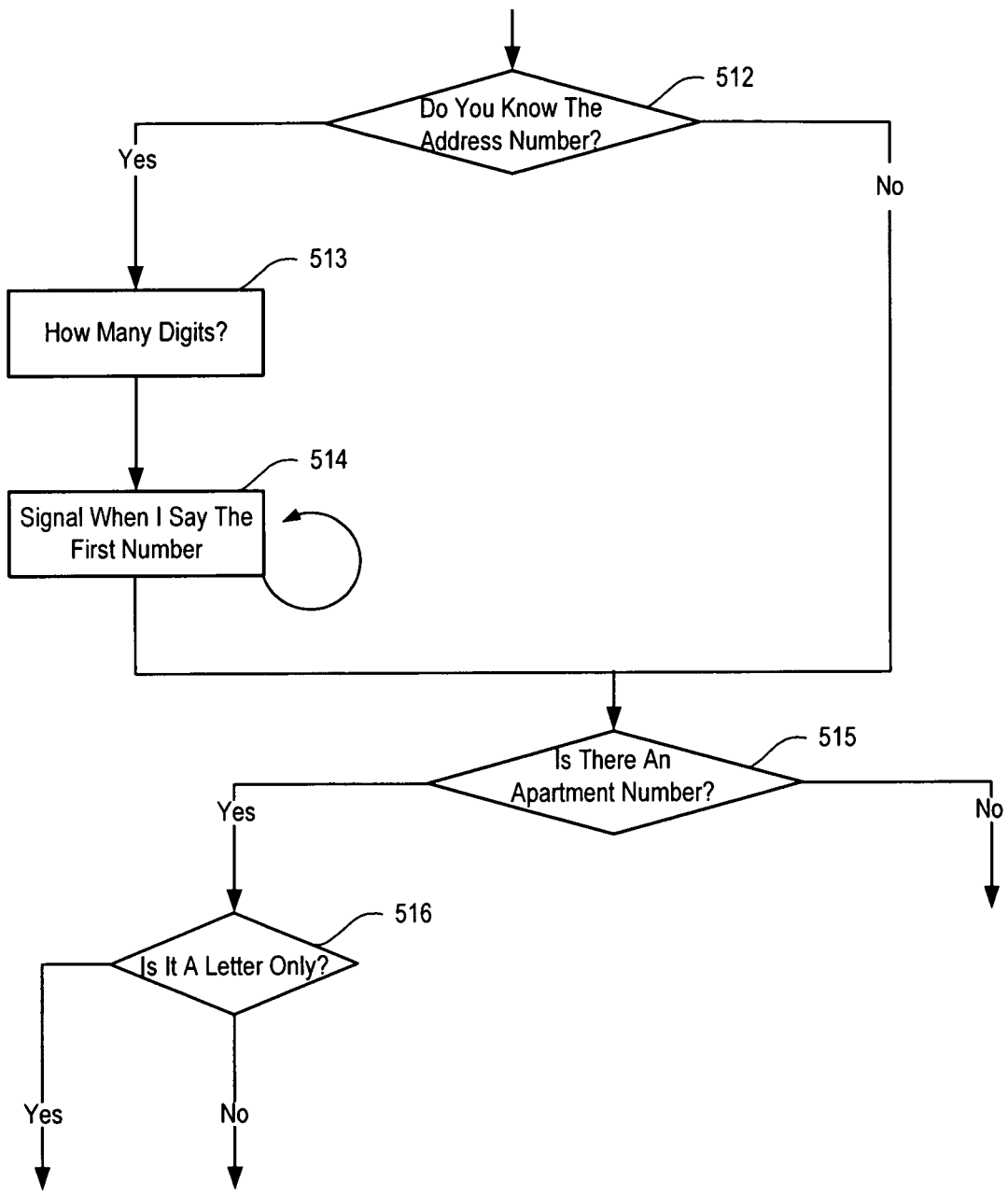
Figure 4P:
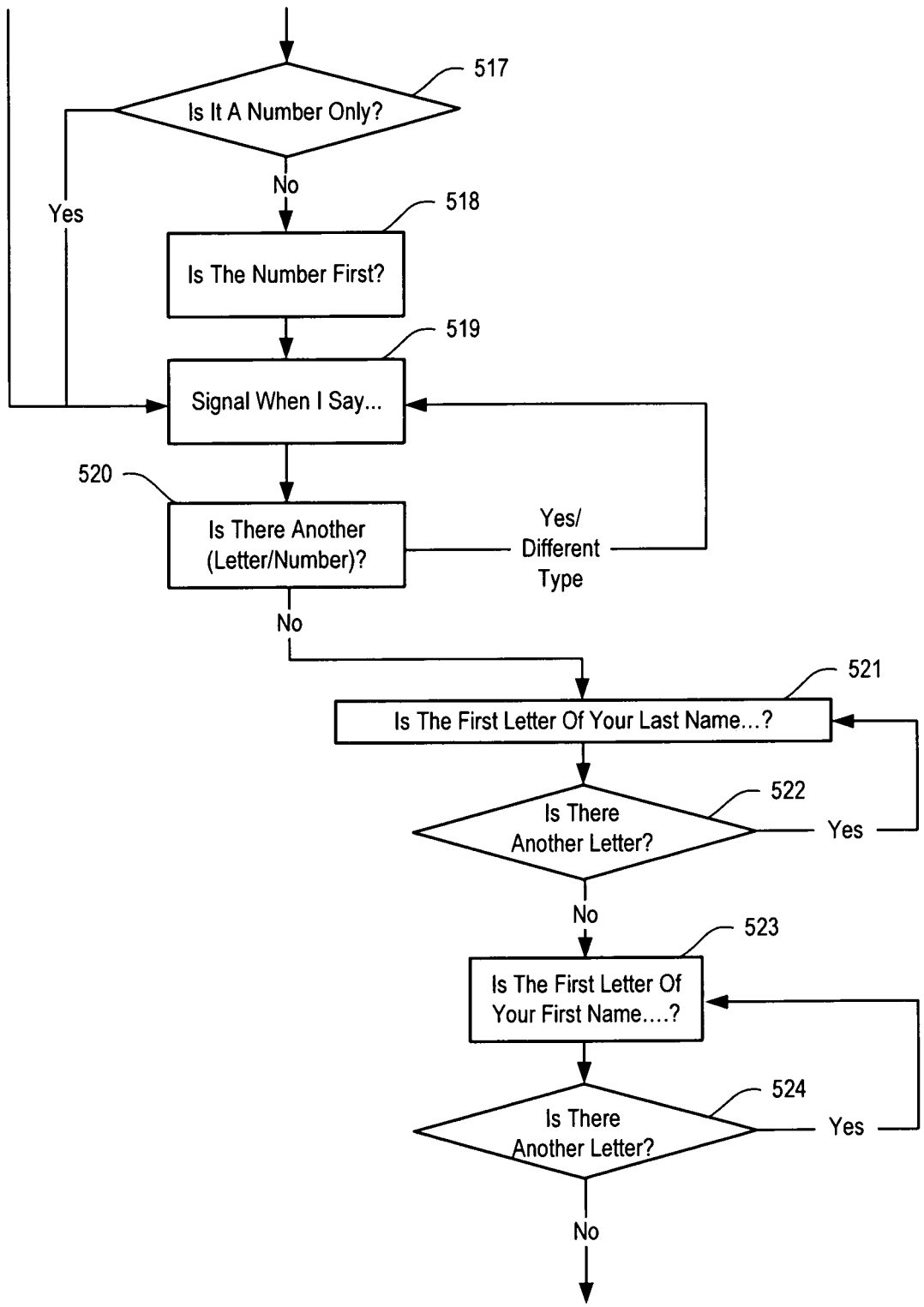
Figure 4Q:
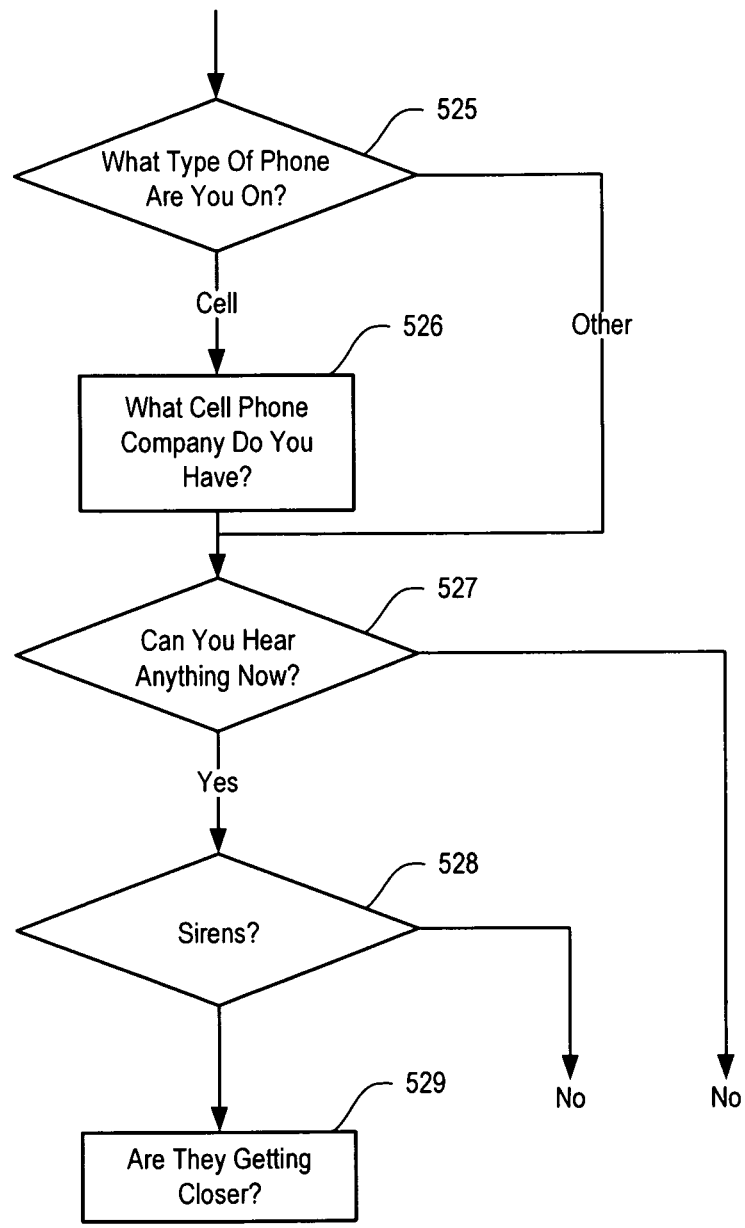

FIGS. 4A-Q are a detailed flow diagram of a method 400 implemented by an emergency dispatch system including a locator diagnostic tool 122 (FIG. 1), according to one embodiment. The locator diagnostic tool 122 may be initialized, typically, from a dispatch protocol 108. The locator diagnostic tool 122 may be launched from the case entry portion of a dispatch protocol 108 and/or a complaint-specific portion of a dispatch protocol 108. As can be appreciated, the locator diagnostic tool 122 may be accessed a variety of ways. In an embodiment, the locator diagnostic tool 122 may initialize once the emergency dispatch protocol 108 has traversed all or a portion of a case entry protocol. Alternatively, or in addition, an emergency dispatch protocol 108 may automatically shunt to the locator diagnostic tool 122 immediately upon receiving indication that the incident location is unknown.

The locator diagnostic tool 122 may present to the dispatcher 104 a series of preprogrammed inquiries. The preprogrammed inquiries may be considered a part of a pre-scripted interrogation that is based on a logical tree of the locator diagnostic tool 122. (The flow diagram of FIGS. 4A-Q may be considered to portray a logical tree, according to one embodiment.) The preprogrammed inquiries that are presented as part of a pre-scripted interrogation may depend on dispatcher-entered input, as will be described. A pre-scripted interrogation may be considered to be a set of preprogrammed inquiries presented according to traversal of a path along the logical tree.

During a pre-scripted interrogation, the locator diagnostic tool 122 may receive input from the dispatcher 104 corresponding to instructions and preprogrammed inquiries, as was explained above with reference to FIG. 3. The input may be received substantially in real time, as the dispatcher 104 provides the input. Alternatively, or in addition, the input may be received from the emergency dispatch system because information sought by the locator diagnostic tool 122 may have previously been obtained from the dispatcher 104 via the case entry protocol and/or another portion of the dispatch protocol 108. Alternatively, or in addition, the input may be received from another diagnostic tool. While explicit steps of receiving information are not depicted in FIGS. 4A-Q, an ordinarily skilled artisan will recognize that input may be received at various points in the method 400 of the locator diagnostic tool 122.

The dispatcher-entered input relates to the emergency call and/or the reported incident. The dispatcher-entered input may affect the path along which the logical tree is traversed. Various paths through one embodiment of a logical tree of a locator diagnostic tool 122 will now be described, including the corresponding preprogrammed inquiries and potential dispatcher-entered input that may be considered.

The emergency dispatch system may begin by presenting 401 a preprogrammed inquiry, "What's the address of your emergency?" The user interface may include a freeform text box to receive input indicating the response, and/or the user interface may provide one or more possible selections. In response to the inquiry, the caller 118 may reply that the caller 118 "doesn't know," "can't say," and/or is otherwise unsure of the incident location. If the input indicates the incident location is not known, the emergency dispatch system may determine that the locator diagnostic tool 122 should be started.

Before starting the locator diagnostic tool 122, the emergency dispatch system may gather more basic information from the caller 118. For example, the emergency dispatch system may provide 402 a preprogrammed inquiry, "What's the phone number you're calling from?" The phone number may be important to gather before starting the locator diagnostic tool 122 in case the call is disconnected before all the information has been gathered. Once any additional information has been gathered, the emergency dispatch system may start 403 the locator diagnostic tool 122. The user interface for the locator diagnostic tool 122 may include a pop-up window containing the inquiries and input components for the locator diagnostic tool 122. (The user interface for the locator diagnostic tool 122 is discussed in further detail below with reference to FIG. 6.)

The locator diagnostic tool 122 may present 404 a preprogrammed inquiry asking what type of phone the caller 118 is calling from. The locator diagnostic tool 122 may present options, such as "Cell," "Home," "Computer," "Payphone," "Satellite Phone," "Ham Radio," "CB Radio," and "Other." The dispatcher 104 may be able to select an option indicative of the caller's response, and/or the dispatcher 104 may select "Other" and input a freeform text response.

Next, the locator diagnostic tool 122 may instruct the dispatcher 104 to gather additional basic information, such as by presenting 405 a preprogrammed inquiry, "Okay, tell me exactly what happened," and presenting 406 a preprogrammed inquiry, "What's your name?" In alternative embodiments, inquiries about the complaint and/or the caller's name may be performed before or after starting 403 the locator diagnostic tool 122. The locator diagnostic tool 122 may provide additional inquiries that the dispatcher 104 can convey to the caller 118 if appropriate, such as presenting 407 a preprogrammed inquiry asking the caller 118 for the caller's social security and/or identification number and presenting 408 a preprogrammed inquiry asking the caller 118 for the caller's license plate number.

The locator diagnostic tool 122 may display 409 an instruction to be conveyed to the caller 118. The instruction may include, "We're going to help you. Listen carefully; I need more information to find out exactly where you are." The locator diagnostic tool 122 may present 410 a preprogrammed inquiry asking whether the caller 118 can speak freely. Predetermined options may be presented to the dispatcher 104, including an option indicating the caller 118 can answer completely/appropriately, an option indicating the caller 118 can answer "Yes" or "No" only, and an option indicating the caller 118 cannot answer. Different paths may be traversed depending on the option selected. If the caller 118 can only answer "Yes" or "No" or cannot answer, a special communications path may be taken. Otherwise, a normal communications path may be taken. The special communications path is discussed in greater detail below.

On the normal communications path, the locator diagnostic tool 122 may present 411 a preprogrammed inquiry, "Describe where you are right now." As part of the inquiry, the locator diagnostic tool 122 may indicate the specific details that should be elicited from the caller 118 by the dispatcher 104, including the state, county, city, area/neighborhood, street, entrance, and building. If the caller 118 indicates that the caller 118 is in a building, the locator diagnostic tool 122 may present 412 a preprogrammed inquiry asking for the type of building. Presented options may include "Business," "Home," Apartment," and "Other." Additionally, the locator diagnostic tool 122 may present 413 a preprogrammed inquiry asking for the number on the building.

The dispatcher 104 may be presented 414 a preprogrammed inquiry regarding the environment type. Predetermined options may include "Urban/Suburban" and "Rural/Wilderness." Different paths in the logical tree may be taken depending on which option is selected. The "Rural/Wilderness" path is discussed in greater detail below. If "Urban/Suburban" is selected, the locator diagnostic tool 122 may present 415 a preprogrammed inquiry, "What else can you see (any landmarks)?" The locator diagnostic tool 122 may accept an input of freeform text. The locator diagnostic tool 122 may present 416 a preprogrammed inquiry as to whether the caller 118 is inside, outside, or underground. Different paths may be taken in the logical tree depending on the dispatcher-entered input of the caller's response. The outside and underground paths are discussed in greater detail below.

If the dispatcher 104 indicates the caller 118 is inside, the locator diagnostic tool 122 may present 417 a preprogrammed inquiry, "Are you in a car?" Preprogrammed response options may include "Yes" and "No." In response to an input of "Yes," the locator diagnostic tool 122 may launch 418 a car description diagnostic to obtain a description of the vehicle. The locator diagnostic tool 122 may also provide 419 an instruction to try to get a GPS position, for example, from a car navigation system. Alternatively, or in addition, the caller 118 may be instructed to connect to a telematics service provider (e.g., OnStar® or Agero®), such as by pushing a button. If a sufficient description of the car is received, a vehicle locator device may be activated by the dispatcher 104 without any action by the caller. Once all car-related questions have been asked, the locator diagnostic tool 122 may skip to step 441.

In response to an input indicating the caller 118 is not in a car, the locator diagnostic tool 122 may present 420 a preprogrammed inquiry, "Are you in a building?" Preprogrammed response options may include "Yes" and "No." If the dispatcher 104 indicates that the caller 118 is not in a building, the locator diagnostic tool 122 may skip to step 441. Otherwise, the locator diagnostic tool 122 may launch 421 a building description diagnostic to obtain a description of the building. Alternatively, or in addition, the dispatcher 104 may be presented with a preprogrammed inquiry, "What type?" The locator diagnostic tool 122 may then present 422 a preprogrammed inquiry, "Are you in your own residence?" Preprogrammed response options may include "Yes" and "No." For an input of "Yes," the locator diagnostic tool 122 may indicate 423 the specific details that should be elicited from the caller 118 by the dispatcher 104 if the caller 118 is in the caller's own residence, including the color and style of the residence, whether a car is in the driveway, whether there is a fence, and the type of building.

The locator diagnostic tool 122 may also present 424 a preprogrammed inquiry, "Can you get a piece of mail and read me the address?" and an indication the inquiry should be asked if appropriate. The presented options may include "Yes," "No," and "Not Appropriate." If the dispatcher 104 indicates the caller 118 can get mail, the locator diagnostic tool 122 may provide 425 an instruction indicating the caller 118 should read the mail to the dispatcher 104. The locator diagnostic tool 122 may automatically end once the address has been inputted, and/or the locator diagnostic tool 122 may allow the dispatcher 104 to select whether to end the locator diagnostic tool 122 or skip to step 441.

If the dispatcher 104 indicates the caller 118 cannot get a piece of mail, the locator diagnostic tool 122 may present 426 a preprogrammed inquiry, "Do you have a house phone (wired, landline)?" and an indication the inquiry should be asked if appropriate. The locator diagnostic tool 122 may present preprogrammed options of "Yes," "No," and "Not Appropriate." If the dispatcher 104 selects "Yes" based on the caller response, the dispatcher 104 may be provided 427 an instruction to convey to the caller 118, "Don't hang up this phone. I want you to go to that phone and call 9-1-1 now. This should help us get your address. Let me know when you've done it. I'll stay on this line with you." It should be understood that various emergency phone numbers may be used instead of or in addition to 9-1-1 depending on the country in which the dispatcher 104 is located. The diagnostic locator tool 122 may automatically end once the landline has been used to call 9-1-1, and/or the dispatcher 104 may manually decide whether to end the diagnostic locator tool 122 or skip to step 441. If the caller 118 does not have a landline phone, the locator diagnostic tool 122 may skip to step 441.

If the caller 118 is not in the caller's own residence, the locator diagnostic tool 122 may present 428 a preprogrammed inquiry, "Are you in someone else's residence?" Options of "Yes" and "No" may be presented to the dispatcher 104. If an input of "Yes" is received, the locator diagnostic tool 122 may indicate 429 the specific details about the residence that should be elicited from the caller 118 by the dispatcher 104, including the color and the style of the residence, whether a car is in the driveway, whether there is a fence, and the type of building. The locator diagnostic tool 122 may also present 430 a preprogrammed inquiry, "Can you get a piece of mail and read me the address?" and an indication the inquiry should be asked if appropriate. The locator diagnostic tool 122 may present preprogrammed options including "Yes," "No," and "Not Appropriate." If the dispatcher 104 selects "Yes," the locator diagnostic tool 122 may provide 431 an instruction indicating the caller 118 should read the mail to the dispatcher 104. The locator diagnostic tool 122 may automatically end once the address has been inputted, and/or the locator diagnostic tool 122 may allow the dispatcher 104 to select whether to end the locator diagnostic tool 122 or skip to step 441.

If the dispatcher 104 indicates the caller 118 cannot get a piece of mail, the locator diagnostic tool 122 may present 432 a preprogrammed inquiry, "Is there a house phone (wired, landline)?" and an indication the inquiry should be asked if appropriate. The locator diagnostic tool 122 may present preprogrammed options of "Yes," "No," and "Not Appropriate." If the dispatcher 104 selects "Yes" based on the caller response, the locator diagnostic tool 122 may provide 433 an instruction, "Don't hang up this phone. I want you to go to that phone and call 9-1-1 now. This should help us get your address. Let me know when you've done it. I'll stay on this line with you." The diagnostic locator tool 122 may automatically end once the landline has been used to call 9-1-1, and/or the dispatcher 104 may manually decide whether to end the diagnostic locator tool 122 or skip to step 441. If the caller 118 cannot access a landline phone, the locator diagnostic tool 122 may skip to step 441. If the caller 118 is not in someone else's residence, the locator diagnostic tool 122 may proceed to step 441.

If, at step 416, the dispatcher 104 indicates the caller 118 is outside, the locator diagnostic tool 122 may provide 434 a request for the caller 118 to describe the location. In an embodiment, possible locations may be provided to the dispatcher 104 and can be suggested to the caller 118 if the caller 118 is having difficulty describing the location. In an alternative embodiment, each possible location may be provided as a yes/no question that can be presented to the caller 118. Possible locations provided by the locator diagnostic tool 122 may include, but are not limited to, in a field, on the sidewalk, on the road, in the forest/trees, in a park, on a trail, by a river, by a canal, in a canyon, near a lake/reservoir, in a parking lot, in a parking garage, at a beach/wharf/pier/dock/boat slip/marina, near a lighthouse, and in a campsite.

If the dispatcher 104 indicates the caller 118 is on a road, the locator diagnostic tool 122 may present 435 a preprogrammed inquiry asking which side, present 436 a preprogrammed inquiry asking whether the road is paved, and present 437 a preprogrammed inquiry asking for the number of lanes. The locator diagnostic tool 122 may accept a freeform text response to each inquiry. If the caller 118 knows the type of location, the locator diagnostic tool 122 may present 438 a preprogrammed inquiry, "Can you see its name?" A freeform text response may be accepted by the locator diagnostic tool 122. The dispatcher 104 may be presented 439 a preprogrammed inquiry, "Does it have a number on it?" and an indication to ask the inquiry if appropriate. The dispatcher 104 may be permitted to enter a freeform text response and/or indicate the inquiry is not appropriate. The locator diagnostic tool 122 may proceed to step 441.

If, at step 416, the dispatcher 104 indicates the caller 118 is underground, the locator diagnostic tool 122 may provide 440 a request for the caller 118 to describe the location. The locator diagnostic tool 122 may indicate possible locations to the dispatcher 104 for suggestion to the caller 118 if the caller 118 is having difficulty describing the location. Alternatively, or in addition, the locator diagnostic tool 122 may provide each possible location as a yes/no question that can be presented to the caller 118. Possible locations to provide to underground callers may include, but are not limited to, in a mine, in a tunnel, in an underground parking garage, in a subway, in a storm drain, in a culvert, in a sewer, in an aqueduct, in a cave, and in a well. The locator diagnostic tool 122 may proceed to step 441.

Once the specific inquiries related to inside, outside, and underground callers have been relayed, the locator diagnostic tool 122 may return to a common set of preprogrammed inquiries. The dispatcher 104 may be presented 441 a preprogrammed inquiry, "Is there anyone near you who could help?" Preprogrammed responses of "Yes" and "No" may be provided to the dispatcher 104. If an input of "Yes" is received, the locator diagnostic tool 122 may present 442 a preprogrammed inquiry, "Can you attract their attention (yell/scream/wave/make noise)?" The locator diagnostic tool 122 may present preprogrammed responses of "Yes" and "No." If the dispatcher 104 inputs a "Yes" response, the locator diagnostic tool 122 may provide 443 an instruction to the dispatcher 104 to convey to the caller 118, "Do it now." Then, the locator diagnostic tool 122 may present 444 a preprogrammed inquiry, "Did they notice you?" The dispatcher 104 may be provided preprogrammed responses of "Yes" and "No." If the caller 118 was noticed, the locator diagnostic tool 122 may provide 445 an instruction to have the caller 118 give the phone to the person. The dispatcher 104 may request the location from the person, and the locator diagnostic tool 122 may automatically end or be manually ended by the dispatcher 104.

If there is no one near the caller 118 and/or the person's attention cannot be attracted, the locator diagnostic tool 122 may present 446 a preprogrammed inquiry, "What landmarks do you see?" The locator diagnostic tool 122 may indicate possible landmarks to the dispatcher 104 for suggestion to the caller 118. Alternatively, or in addition, the locator diagnostic tool 122 may provide each possible landmark as a yes/no question that can be presented to the caller 118. Possible landmarks to suggest to the caller 118 may include, but are not limited to, a sign, a billboard, a parking lot, a business, a school, a mile marker, a road, an elevated roadway, a rest stop, a trail, a trail marker, a gate, a mountain, a lake, a reservoir, a dam, a wind turbine, a power line, a bridge, a river, a ski area, a cabin, a train track, a trestle, a wall, a tower, a smokestack, a fence, and a bridge. The locator diagnostic tool 122 may also allow input of freeform text for other landmarks.

If the caller 118 does not indicate any landmarks, the locator diagnostic tool 122 may provide 447 an instruction "Now look: straight ahead, to your left, to your right, behind you, above you, and down." Next, the dispatcher 104 may be provided 448 an instruction to convey to the caller 118, "Tell me what you see." Alternatively, or in addition, a separate question may be presented to the caller 118 for each direction that the caller 118 is instructed to look. If the caller 118 indicates a landmark, the locator diagnostic tool 122 may present 449 a preprogrammed inquiry, "What is its name?" and may present 450 a preprogrammed inquiry, "Does it have a number on it?" The dispatcher 104 may also be presented 451 a preprogrammed inquiry, "What kind of structure is it?" The locator diagnostic tool 122 may indicate possible structures, and/or the locator diagnostic tool 122 may provide each possible structure as a yes/no question that can be presented to the caller 118. Possible structures indicated by the locator diagnostic tool 122 may include, but are not limited to, a tower, a bridge, a sign, a wall, an elevated roadway or track, a river, a park, and a street.

The locator diagnostic tool 122 may present 452 a preprogrammed inquiry, "Can you hear anything now?" Possible sounds may be presented to the dispatcher 104 for suggestion to the caller 118, and/or the locator diagnostic tool 122 may present each possible sound as a separate yes/no question to be conveyed to the caller 118. Possible sounds to suggest to the caller 118 may include, but are not limited to, sirens, people, music, bells, buzzers, machinery, man-made noises, vehicles, planes, trains, animal noises, and water. For certain sounds, such as people, animal noises, and water, the locator diagnostic tool 122 may present 453 a follow-up preprogrammed inquiry, "What type?" A freeform text response may be accepted by the user interface.

Regardless of the response to the inquiry about what the caller 118 can hear, the locator diagnostic tool 122 may present 454a-c a preprogrammed inquiry, "What is the caller's talking status?" that the dispatcher 104 should respond to but not convey to the caller 118. Questions directed to the dispatcher 104 may be indicated, or otherwise differentiated from questions directed to the caller 118, so as to clearly convey to the dispatcher 104 which questions are to be conveyed to the caller 118. For example, questions to the dispatcher 104 may be presented in a different color, such as blue, than the color in which caller questions are presented, such as black. Possible responses presented to the dispatcher 104 may include, but are not limited to, normal/clear; labored breathing; severe pain; not alert speech; can't say what they want to say, but words spoken are clear; garbled speech (unintelligible); can't talk because under duress/fear/danger; and language barrier. If the words are clear but the caller 118 cannot say what he or she wants to say, this may indicate a possible stroke. Garbled speech may indicate a possible stroke and/or that the caller 118 is not alert. The locator diagnostic tool 122 may indicate the possibility of a stroke to the dispatcher 104. If there is a language barrier, the locator diagnostic tool 122 may recommend that the dispatcher 104 consider using a translator (e.g., Language Line Solutions[SM]).

If the dispatcher 104 did not indicate that the caller 118 can hear sirens, the locator diagnostic tool 122 may automatically end, and/or the dispatcher 104 may be able to select whether to end the locator diagnostic tool 122. The locator diagnostic tool 122 may save the caller's responses for later use when searching for the caller 118. If the input indicates the caller 118 can hear sirens, the locator diagnostic tool 122 may present 455 a preprogrammed inquiry, "Where are they coming from?" Preprogrammed responses may include "to your right," "to your left," "in front of you," and "in back of you." The dispatcher 104 may provide the preprogrammed responses to the caller 118 as suggestions or possible answers, and/or the diagnostic locator tool 122 may present each preprogrammed response as a separate yes/no question.

The locator diagnostic tool 122 may present 456 a follow-up preprogrammed inquiry asking for the direction identified. The follow-up inquiry may ask, "Which direction is that?" and provide possible responses of north, east, south, and west, and/or the follow-up inquiry may present a separate inquiry for each direction. If the input from the dispatcher 104 did not indicate that the caller 118 is unsure of the direction, the locator diagnostic tool 122 may automatically end, and/or the dispatcher 104 may be able to manually end the locator diagnostic tool 122. The locator diagnostic tool 122 may save the caller's responses for later use when searching for the caller 118. Alternatively, or in addition, if the caller 118 hears sirens, the dispatcher 104 may continue to ask about their direction until the caller 118 is located.

If the caller 118 is unsure of the direction of the sirens, the locator diagnostic tool 122 may present 457 a preprogrammed inquiry, "Do you know what direction from you north is?" If the input indicates the caller 118 does not know which direction is north, the locator diagnostic tool 122 may provide instructions for determining which way is north so the caller 118 can identify the direction of the sirens. Once instructions for finding north have been presented and any follow-up information input, the locator diagnostic tool 122 may automatically end, and/or the dispatcher 104 may be able to manually end the locator diagnostic tool 122. The locator diagnostic tool 122 may save the caller's responses for later use when trying to find the caller 118.

If the dispatcher 104 selects "Rural/Wilderness" when the locator diagnostic tool 122 presents 414 the preprogrammed inquiry regarding environment type, the locator diagnostic tool 122 may present 458 a preprogrammed inquiry, "Where did you start?" The dispatcher 104 may be able to input freeform text to respond to the inquiry. The locator diagnostic tool 122 may present 459 a preprogrammed inquiry, "Where were you going?" The diagnostic locator tool 122 may accept a freeform text response. The dispatcher 104 may also be presented 460 with a preprogrammed inquiry, "Does anyone know where you are or where you were going?" A freeform text response may be accepted by the locator diagnostic tool 122.

The locator diagnostic tool 122 may present 461 a preprogrammed inquiry, "What can you see (any landmarks)?" The locator diagnostic tool 122 may accept an input of freeform text. The locator diagnostic tool 122 may present 462 a preprogrammed inquiry as to whether the caller 118 is inside, outside, or underground. Different paths may be taken in the logical tree depending on the dispatcher-entered input of the caller's response. The outside and underground paths are discussed in greater detail below.

If the dispatcher 104 indicates the caller 118 is inside, the locator diagnostic tool 122 may present 463 a preprogrammed inquiry, "Are you in a car?" Preprogrammed response options may include "Yes" and "No." In response to an input of "Yes," the locator diagnostic tool 122 may launch 464 a car description diagnostic to obtain a description of the vehicle. The locator diagnostic tool 122 may also provide 465 an instruction to try to get a GPS position, for example, from a car navigation system. Alternatively, or in addition, the caller 118 may be instructed to connect to a telematics service provider (e.g., OnStar® or Agero®), such as by pushing a button. If a sufficient description of the car is received, a vehicle locator device may be activated by the dispatcher 104 without any action by the caller. Once all car-related questions have been asked, the locator diagnostic tool 122 may skip to step 487.

In response to an input indicating the caller 118 is not in a car, the locator diagnostic tool 122 may present 466 a preprogrammed inquiry, "Are you in a building?" Preprogrammed response options may include "Yes" and "No." If the dispatcher 104 indicates that the caller 118 is not in a building, the locator diagnostic tool 122 may skip to step 487. Otherwise, the locator diagnostic tool 122 may launch 467 a building description diagnostic to obtain a description of the building. Alternatively, or in addition, the dispatcher 104 may be presented with a preprogrammed inquiry, "What type?" The locator diagnostic tool 122 may then present 468 a preprogrammed inquiry, "Are you in your own residence?" Preprogrammed response options may include "Yes" and "No." For an input of "Yes," the locator diagnostic tool 122 may indicate 469 the specific details that should be elicited from the caller 118 by the dispatcher 104 if the caller 118 is in the caller's own residence, including the color and style of the residence, whether a car is in the driveway, whether there is a fence, and the type of building.

The locator diagnostic tool 122 may also present 470 a preprogrammed inquiry, "Can you get a piece of mail and read me the address?" and an indication the inquiry should be asked if appropriate. The presented options may include "Yes," "No," and "Not Appropriate." If the dispatcher 104 indicates the caller 118 can get mail, the locator diagnostic tool 122 may provide 471 an instruction indicating the caller 118 should read the mail to the dispatcher 104. The locator diagnostic tool 122 may automatically end once the address has been inputted, and/or the locator diagnostic tool 122 may allow the dispatcher 104 to select whether to end the locator diagnostic tool 122 or skip to step 487.

If the dispatcher 104 indicates the caller 118 cannot get a piece of mail, the locator diagnostic tool 122 may present 472 a preprogrammed inquiry, "Do you have a house phone (wired, landline)?" and an indication the inquiry should be asked if appropriate. The locator diagnostic tool 122 may present preprogrammed options of "Yes," "No," and "Not Appropriate." If the dispatcher 104 selects "Yes" based on the caller response, the dispatcher 104 may be provided 473 an instruction to convey to the caller 118, "Don't hang up this phone. I want you to go to that phone and call 9-1-1 now. This should help us get your address. Let me know when you've done it. I'll stay on this line with you." It should be understood that various emergency phone numbers may be used instead of or in addition to 9-1-1 depending on the country in which the dispatcher 104 is located. The diagnostic locator tool 122 may automatically end once the landline has been used to call 9-1-1, and/or the dispatcher 104 may manually decide whether to end the diagnostic locator tool 122 or skip to step 487. If the caller 118 does not have a landline phone, the locator diagnostic tool 122 may skip to step 487.

If the caller 118 is not in the caller's own residence, the locator diagnostic tool 122 may present 474 a preprogrammed inquiry, "Are you in someone else's residence?" Options of "Yes" and "No" may be presented to the dispatcher 104. If an input of "Yes" is received, the locator diagnostic tool 122 may indicate 475 the specific details about the residence that should be elicited from the caller 118 by the dispatcher 104, including the color and style of the residence, whether a car is in the driveway, whether there is a fence, and the type of building. The locator diagnostic tool 122 may also present 476 a preprogrammed inquiry, "Can you get a piece of mail and read me the address?" and an indication the inquiry should be asked if appropriate. The locator diagnostic tool 122 may present preprogrammed options including "Yes," "No," and "Not Appropriate." If the dispatcher 104 selects "Yes," the locator diagnostic tool 122 may provide 477 an instruction indicating the caller 118 should read the mail to the dispatcher 104. The locator diagnostic tool 122 may automatically end once the address has been inputted, and/or the locator diagnostic tool 122 may allow the dispatcher 104 to select whether to end the locator diagnostic tool 122 or skip to step 487.

If the dispatcher 104 indicates the caller 118 cannot get a piece of mail, the locator diagnostic tool 122 may present 478 a preprogrammed inquiry, "Is there a house phone (wired, landline)?" and an indication the inquiry should be asked if appropriate. The locator diagnostic tool 122 may present preprogrammed options of "Yes," "No," and "Not Appropriate." If the dispatcher 104 selects "Yes" based on the caller response, the locator diagnostic tool 122 may provide 479 an instruction, "Don't hang up this phone. I want you to go to that phone and call 9-1-1 now. This should help us get your address. Let me know when you've done it. I'll stay on this line with you." The diagnostic locator tool 122 may automatically end once the landline has been used to call 9-1-1, and/or the dispatcher 104 may manually decide whether to end the diagnostic locator tool 122 or skip to step 487. If the caller 118 does not have access to a landline phone, the locator diagnostic tool 122 may skip to step 487. If the caller 118 is not in someone else's residence, the locator diagnostic tool 122 may proceed to step 487.

If, at step 462, the dispatcher 104 indicates the caller 118 is outside, the locator diagnostic tool 122 may provide 480 a request for the caller 118 to describe the location. In an embodiment, possible locations may be provided to the dispatcher 104 and can be suggested to the caller 118 if the caller 118 is having difficulty describing the location. In an alternative embodiment, each possible location may be provided as a yes/no question that can be presented to the caller 118. Possible locations provided by the locator diagnostic tool 122 may include, but are not limited to, in a field, on the sidewalk, on the road, in the forest/trees, in a park, on a trail, by a river, by a canal, in a canyon, near a lake/reservoir, in a parking lot, in a structure (e.g., barn garage, coop, silo, manure pit, well), at a beach/wharf/pier/dock/boat slip/marina, near a lighthouse, in a campsite, and at a ski resort/hill/trail.

If the dispatcher 104 indicates the caller 118 is on a road, the locator diagnostic tool 122 may present 481 a preprogrammed inquiry asking which side, present 482 a preprogrammed inquiry asking whether the road is paved, and present 483 a preprogrammed inquiry asking for the number of lanes. The locator diagnostic tool 122 may accept a freeform text response to each inquiry. If the caller 118 knows the type of location, the locator diagnostic tool 122 may present 484 a preprogrammed inquiry, "Can you see its name?" A freeform text response may be accepted by the locator diagnostic tool 122. The dispatcher 104 may be presented 485 a preprogrammed inquiry, "Does it have a number on it?" and an indication to ask the inquiry if appropriate. The dispatcher 104 may be permitted to enter a freeform text response and/or indicate the inquiry is not appropriate. The locator diagnostic tool 122 may proceed to step 487.

If, at step 462, the dispatcher 104 indicates the caller 118 is underground, the locator diagnostic tool 122 may provide 486 a request for the caller 118 to describe the location. The locator diagnostic tool 122 may indicate possible locations to the dispatcher 104 for suggestion to the caller 118 if the caller 118 is having difficulty describing the location. Alternatively, or in addition, the locator diagnostic tool 122 may provide each possible location as a yes/no question that can be presented to the caller 118. Possible locations to provide to underground callers may include, but are not limited to, in a mine, in a tunnel, in a cellar, in a crawl space, in a storm drain, in a culvert, in a sewer, in an aqueduct, in a cave, and in a well. The locator diagnostic tool 122 may proceed to step 487.

Once the specific inquiries related to inside, outside, and underground callers have been relayed, the locator diagnostic tool 122 may return to a common set of preprogrammed inquiries. The dispatcher 104 may be presented 487 a preprogrammed inquiry, "Is there anyone near you who could help?" Preprogrammed responses of "Yes" and "No" may be provided to the dispatcher 104. If an input of "Yes" is received, the locator diagnostic tool 122 may present 488 a preprogrammed inquiry, "Can you attract their attention (yell/scream/wave/make noise)?" The locator diagnostic tool 122 may present preprogrammed responses of "Yes" and "No." If the dispatcher 104 inputs a "Yes" response, the locator diagnostic tool 122 may provide 489 an instruction to the dispatcher 104 to convey to the caller 118, "Do it now." Then, the locator diagnostic tool 122 may present 490 a preprogrammed inquiry, "Did they notice you?" The dispatcher 104 may be provided preprogrammed responses of "Yes" and "No." If the caller 118 was noticed, the locator diagnostic tool 122 may provide 491 an instruction to have the caller 118 give the phone to the person. The dispatcher 104 may request the location from the person, and the locator diagnostic tool 122 may automatically end or be manually ended by the dispatcher 104.

If there is no one near the caller 118 and/or the person's attention cannot be attracted, the locator diagnostic tool 122 may present 492 a preprogrammed inquiry, "What landmarks do you see?" The locator diagnostic tool 122 may indicate possible landmarks to the dispatcher 104 for suggestion to the caller 118. Alternatively, or in addition, the locator diagnostic tool 122 may provide each possible landmark as a yes/no question that can be presented to the caller 118. Possible landmarks to suggest to the caller 118 may include, but are not limited to, a sign, a billboard, a parking lot, a business, a school, a mile marker, a road, an elevated roadway, a rest stop, a trail, a trail marker, a gate, a mountain, a lake, a reservoir, a dam, a wind turbine, a power line, a bridge, a river, a ski area, a cabin, a train track, a trestle, a wall, a tower, a smokestack, a fence, and a bridge. The locator diagnostic tool 122 may also allow input of freeform text for other landmarks.

If the caller 118 does not indicate any landmarks, the locator diagnostic tool 122 may provide 493 an instruction "Now look: straight ahead, to your left, to your right, behind you, above you, and down." Next, the dispatcher 104 may be provided 494 an instruction to convey to the caller 118, "Tell me what you see." Alternatively, or in addition, a separate question may be presented to the caller 118 for each direction that the caller 118 is instructed to look. If the caller 118 indicates a landmark, the locator diagnostic tool 122 may present 495 a preprogrammed inquiry, "What is its name?" and may present 496 a preprogrammed inquiry, "Does it have a number on it?"

The locator diagnostic tool 122 may present 497 a preprogrammed inquiry, "Can you hear anything now?" Possible sounds may be presented to the dispatcher 104 for suggestion to the caller 118, and/or the locator diagnostic tool 122 may present each possible sound as a separate yes/no question to be conveyed to the caller 118. Possible sounds to suggest to the caller 118 may include, but are not limited to, sirens, people, music, bells, buzzers, machinery, man-made noises, vehicles, planes, trains, animal noises, and water. For certain sounds, such as people, animal noises, and water, the locator diagnostic tool 122 may present 498 a follow-up preprogrammed inquiry, "What type?" A freeform text response may be accepted by the user interface.

Regardless of the response to the inquiry about what the caller 118 can hear, the locator diagnostic tool 122 may present 499*a-c* a preprogrammed inquiry, "What is the caller's talking status?" that the dispatcher 104 should respond to but not convey to the caller 118. Possible responses presented to the dispatcher 104 may include, but are not limited to, normal/clear; labored breathing; severe pain; not alert speech; can't say what they want to say, but words spoken are clear; garbled speech (unintelligible); can't talk because under duress/fear/danger; and language barrier. If the words are clear but the caller 118 cannot say what he or she wants to say, this may indicate a possible stroke. Garbled speech may indicate a possible stroke and/or that the caller 118 is not alert. The locator diagnostic tool 122 may indicate the possibility of a stroke to the dispatcher 104. If there is a language barrier, the locator diagnostic tool 122 may recommend that the dispatcher 104 consider using a translator (e.g., Language Line Solutions$^{SM}$).

If the dispatcher 104 did not indicate that the caller 118 can hear sirens, the locator diagnostic tool 122 may automatically end, and/or the dispatcher 104 may be able to select whether to end the locator diagnostic tool 122. The locator diagnostic tool 122 may save the caller's responses for later use when searching for the caller 118. If the input indicates the caller 118 can hear sirens, the locator diagnostic tool 122 may present 500 a preprogrammed inquiry, "Where are they coming from?" Preprogrammed responses may include "to your right," "to your left," "in front of you," and "in back of you." The dispatcher 104 may provide the preprogrammed responses to the caller 118 as suggestions or possible answers, and/or the diagnostic locator tool 122 may present each preprogrammed response as a separate yes/no question.

The locator diagnostic tool 122 may present 501 a follow-up preprogrammed inquiry asking for the direction identified. The follow-up inquiry may ask, "Which direction is that?" and provide possible responses of north, east, south, and west, and/or the follow-up inquiry present a separate inquiry for each direction. If the input from the dispatcher 104 did not indicate that the caller 118 is unsure of the direction, the locator diagnostic tool 122 may automatically end, and/or the dispatcher 104 may be able to manually end the locator diagnostic tool 122. The locator diagnostic tool 122 may save the caller's responses for later use when searching for the caller 118. Alternatively, or in addition, if the caller 118 hears sirens, the dispatcher 104 may continue to ask about their direction until the caller 118 is located.

If the caller 118 is unsure of the direction of the sirens, the locator diagnostic tool 122 may present 502 a preprogrammed inquiry, "Do you know what direction from you north is?" If the input indicates the caller 118 does not know which direction is north, the locator diagnostic tool 122 may provide instructions for determining which way is north so the caller 118 can identify the direction of the sirens. If the caller 118 is not unsure of the direction of the sirens and/or once instructions for finding north have been presented and any follow-up information input, the locator diagnostic tool 122 may automatically end, and/or the dispatcher 104 may be able to manually end the locator diagnostic tool 122. The locator diagnostic tool 122 may save the caller's responses for later use when trying to find the caller 118.

If the caller 118 can only answer "Yes" or "No" or cannot answer, a special communications path may be taken. The locator diagnostic tool 122 may provide 503 an instruction explaining signal types for the dispatcher 104 to convey to the caller 118, such as, "So we can communication and find you, signal me any way you can when the answer to anything I ask is 'Yes.' You can tap, cough, blow into the phone, push a number button on the phone, or say 'okay,' or any other word. Give me the signal you want to use so we can begin."

The locator diagnostic tool 122 may present 504 a preprogrammed inquiry, "What kind of place is this? Is it a house? Apartment building? Business? Duplex? Trailer? Cabin? Something else?" The dispatcher 104 may indicate the response signaled by the caller 118, for example, by selecting a corresponding input. If the dispatcher 104 inputs that the place is something else, the locator diagnostic tool 122 may ask broader questions to determine the location. For example, the locator diagnostic tool 122 may initially attempt to determine whether the caller 118 is in a building, which may be the most likely location for the caller 118, and then the locator diagnostic tool 122 may traverse a "20 Questions" style logical tree. The "20 Questions" style logical tree may start with broad questions and traverse the tree to narrower questions based on previous responses.

The locator diagnostic tool 122 may present 505 a preprogrammed inquiry, "What kind of a street is this? Is it a freeway? Multi-lane highway? Two-lane street? One-way street? Alley? Side Street? Dirt Road? Something else?" The locator diagnostic tool 122 may ask about both buildings and streets before traversing a "20 Questions" style logical tree, and/or the locator diagnostic tool 122 may traverse the "20 Questions" style logical tree if a response of "something else" is received for either inquiry.

The locator diagnostic tool 122 may present 506 a preprogrammed inquiry, "Do you know the street name you're on/near?" If the dispatcher 104 indicates that the caller 118 signaled "Yes," the locator diagnostic tool 122 may present 507 a preprogrammed inquiry, "Is it a word?" If a "Yes" response is received, the dispatcher 104 may be provided 508 with an instruction, "I'm going to help you spell it. Signal when I hit the first letter: A, B, C . . . ." The locator diagnostic tool 122 may instruct the dispatcher 104 to confirm the letter by saying, e.g., "Is 'C' correct?" The locator diagnostic tool 122 may present 509 a preprogrammed inquiry, "Is there another letter?" The dispatcher 104 may be instructed to continue signaling letters until the entire street name has been spelled out.

If the response indicates the street name is not a word, the locator diagnostic tool 122 may present 510 an inquiry, "How many digits are there in the street name: 1, 2, 3 . . . ." The locator diagnostic tool 122 may provide 511 an instruction, "Signal when I say the first number: 1, 2, 3 . . . ." The locator diagnostic tool 122 may continue to instruct the dispatcher 104 to request digits from the street name until every digit has been input by the dispatcher 104.

Once the street name has been received and/or if the street name is not known, the locator diagnostic tool 122 may present 512 an inquiry, "Do you know the address number you're at/near?" Preprogrammed responses may include "Yes" and "No." If the dispatcher 104 inputs "Yes," the dispatcher 104 may be presented 513 a preprogrammed inquiry, "How many digits are in the address number: 1, 2, 3 . . . ." Once a response is received, the locator diagnostic tool 122 may provide 514 an instruction, "Okay, I'm going to help you tell me. Signal when I hit the first number: 1, 2, 3 . . . ." The locator diagnostic tool 122 may instruct the dispatcher 104 to confirm the number by saying, e.g., "Is '3' correct?"

Once the address number has been received and/or if the address number is not known, the locator diagnostic tool 122 may present 515 a preprogrammed inquiry, "Is there an apartment number you're in?" The locator diagnostic tool 122 may present preprogrammed responses of "Yes" and "No." If an input of "Yes" is received, the locator diagnostic tool 122 may present 516 a preprogrammed inquiry, "Is it a letter only?" Preprogrammed responses may include "Yes" and "No." If the dispatcher 104 indicates the response is "No," the locator diagnostic tool 122 may present 517 a preprogrammed inquiry, "Is it a number only?" The locator diagnostic tool 122 may accept preprogrammed responses of "Yes" or "No." If the dispatcher 104 indicates the response is "No," the locator diagnostic tool 122 may instruct the dispatcher 104 to confirm it is both letters and numbers. The dispatcher 104 may be presented 518 a preprogrammed inquiry, "Is the number first?" The dispatcher 104 may also be presented preprogrammed responses of "Yes" and "No."

Once the locator diagnostic tool 122 has determined whether the apartment number is letters only or numbers only, or whether the numbers or letters come first, the locator diagnostic tool 122 may present 519 a preprogrammed inquiry, "Signal when I say the first [number/letter]: [1/2, 1, 2, 3 . . . /A, B, C . . . ]." The locator diagnostic tool 122 may determine whether to use letters or numbers in the preprogrammed inquiry based on the responses to previous inquiries. After receiving the first letter/number, the locator diagnostic tool 122 may present 520 a preprogrammed inquiry, "Is there another [number/letter]?" Preprogrammed responses may include "Yes" and "No." If the response is "Yes" and/or the response is "No" but only numbers or letters have been received in an apartment number containing both numbers and letters, the locator diagnostic tool 122 may instruct the dispatcher 104 to signal additional numbers/letters until the full apartment number is received.

Once the apartment number has been received and/or if the caller 118 does not provide an apartment number, the locator diagnostic tool 122 may present 521 a preprogrammed inquiry "I'm going to help you spell your last name. Signal when I hit the first letter: A, B, C . . . ." When a response is received, the locator diagnostic tool 122 may indicate the dispatcher 104 should confirm the response, such as by presenting a preprogrammed inquiry, "Is 'C' correct?" The locator diagnostic tool 122 may present 522 a preprogrammed inquiry, "Is there another letter?" The locator diagnostic tool 122 may instruct the dispatcher 104 to continue signaling letters until the caller's last name has been spelled.

Once the caller's last name has been spelled, the locator diagnostic tool 122 may present 523 a preprogrammed inquiry, "I'm going to help you spell your first name. Signal when I hit the first letter: A, B, C . . . " When the dispatcher 104 inputs a response, the locator diagnostic tool 122 may instruct the dispatcher 104 to confirm the response, for example, by presenting a preprogrammed inquiry, "Is 'C' correct?" The locator diagnostic tool 122 may present 524 a preprogrammed inquiry, "Is there another letter?" The locator diagnostic tool 122 may continue to present inquiries until the caller's first name has been spelled. In an embodiment, the locator diagnostic tool 122 may not present 524 the preprogrammed inquiry, "Is there another letter?" and may instead continue requesting letters until the dispatcher 104 indicates the name seems complete. Once the dispatcher 104 indicates the name seems complete, the locator diagnostic tool 122 may present 524 the preprogrammed inquiry, "Is there another letter?"

The locator diagnostic tool 122 may present 525 a preprogrammed inquiry, "What type of phone are you on? Is it a cell phone? Wired phone? Payphone? Computer? Satellite phone? CB radio? Ham radio? Voice over IP (VOIP) phone?" The locator diagnostic tool 122 may indicate to the dispatcher 104 that the inquiry should only be conveyed to the caller 118 if appropriate. If the dispatcher 104 indicates that the caller 118 has a cell phone, the locator diagnostic tool 122 may present 526 a preprogrammed inquiry "What phone company do you have? Is it AT&T? Verizon? T-Mobile? Sprint? Nextel? Cricket? Vonage? Qwest? TracFone? U.S. Cellular? nTelos? Clearwire? Boost Mobile?"

The locator diagnostic tool 122 may present 527 a preprogrammed inquiry, "Can you hear anything now?" Preprogrammed responses may include "Yes" and "No." If the dispatcher 104 indicates the caller 118 signaled "Yes," the locator diagnostic tool 122 may list various possible sounds, such as presenting 528 a preprogrammed inquiry "Is it a siren?" If the dispatcher 104 indicates the caller 118 can hear a siren, the locator diagnostic tool 122 may present 529 a preprogrammed inquiry, "Tell me when the sirens are getting closer (or farther away). Tap once for closer, twice for farther away." In an embodiment, the dispatcher 104 may also, or instead, ask about lights from an emergency responder and whether they are getting closer or farther away. In an embodiment, the dispatcher 104 may continue to ask about the sirens until the caller 118 is located.

Once the dispatcher 104 has indicated whether the sirens are getting closer and/or if the dispatcher 104 has indicated that the caller 118 does not hear sirens, the locator diagnostic tool 122 may automatically end, and/or the dispatcher 104 may be able to manually end the locator diagnostic tool 122. The locator diagnostic tool 122 may save the caller's responses for later use when searching for the caller 118. Before ending, the locator diagnostic tool 122 may provide an instruction for the dispatcher 104 to convey to the caller 118 indicating that the information provided by the caller 118 is being saved and the dispatcher 104 will be asking additional questions about the emergency. The emergency dispatch system may return to the emergency dispatch protocol 108 once the locator diagnostic tool 122 ends. Those of skill in the art will recognize that many changes may be made to the special communications path. For example, any of the questions from the normal communications path may be converted to yes/no questions and used as part of the special communications path.

If the dispatcher 104 indicates that emergency responders are close to the caller 118, the locator diagnostic tool 122 may provide "Find Me" instructions to the dispatcher 104 to convey to the caller 118. The locator diagnostic tool 122 may automatically decide to provide the "Find Me" instructions if the caller 118 indicates sirens are nearby, and/or the dispatcher 104 may be able to manually select a user input, such as a button or tab, to display the "Find Me" instructions. The "Find Me" instructions may include, "I want you to make yourself visible or heard—as long as it's appropriate with your condition or situation. If you can: open a door; scream when you hear something; make noise: whistle, pound on something (walls, pipes, trees); wave your arms; flash some lights: headlights/hazard lights/brake lights/interior lights; push your car's alarm or panic button; turn on the windshield wipers; (if by the road) get out to the edge of the road; crank up the stereo, radio, TV; trigger your house/burglar alarm; trigger your car panic alarm; blow a whistle; flash a mirror."

The locator diagnostic tool 122 may also provide rules, axioms, and/or information to the dispatcher 104, for example, on an alternate tab. The rules may include:

"1) Get a supervisor or team member to assist early on to manage logistics (maps, additional unit management) and direct the communication between the dispatcher and dispatch positions.
2) Relay full information known as obtained at key points to the responders. Don't filter information. You may not know exactly what the value of some information is to the responders or scene commander.
3) The caller's car or a nearby car may have a telematic service provider button installed, such as OnStar® or Agero®. If safe to do so, advise them to push this button to activate.
4) When using special communications methods, match your spelling/numbering speed to the signaling method and/or caller's ability.
5) If battery charge is low or extended time anticipated to reach the caller, establish a callback schedule to conserve battery power."

The axioms may include:

"1) There may be a medical alerting device nearby that a confused or distraught caller might have forgotten to use.
2) This Locator Diagnostic Tool is designed to work in concert with the agency's related standard operational procedure (SOP). This SOP should be reviewed again when this Locator Diagnostic Tool is implemented."

The locator diagnostic tool 122 may include critical emergency dispatch information and additional information. The critical emergency dispatch information may include, "Be aware of the caller's cell phone battery charge level and charger availability." The additional information may include the characteristics of expressive aphasia associated with strokes. The additional information may include, "Words the caller says are clear, but they can't say much of what they want to say; They don't know what's happened to them; They get frustrated or angry; They can't say certain things: big words, complex words, uncommon words; Can tap, say simple and very common words."

Figure 5A:
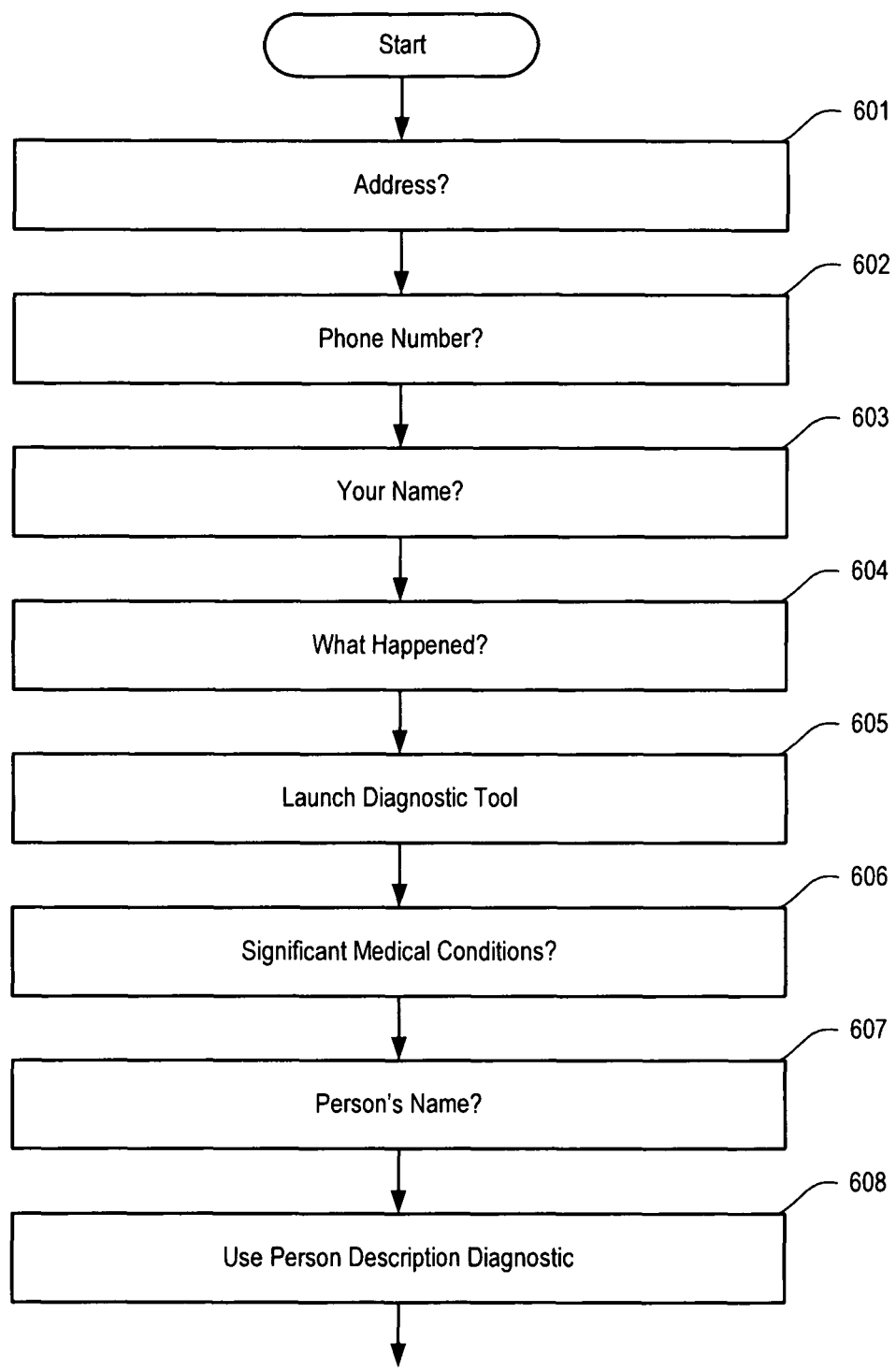
FIGS. 5A-C are a detailed flow diagram of a method of a locator diagnostic tool for an emergency dispatch system, according to one embodiment
Figure 5B:
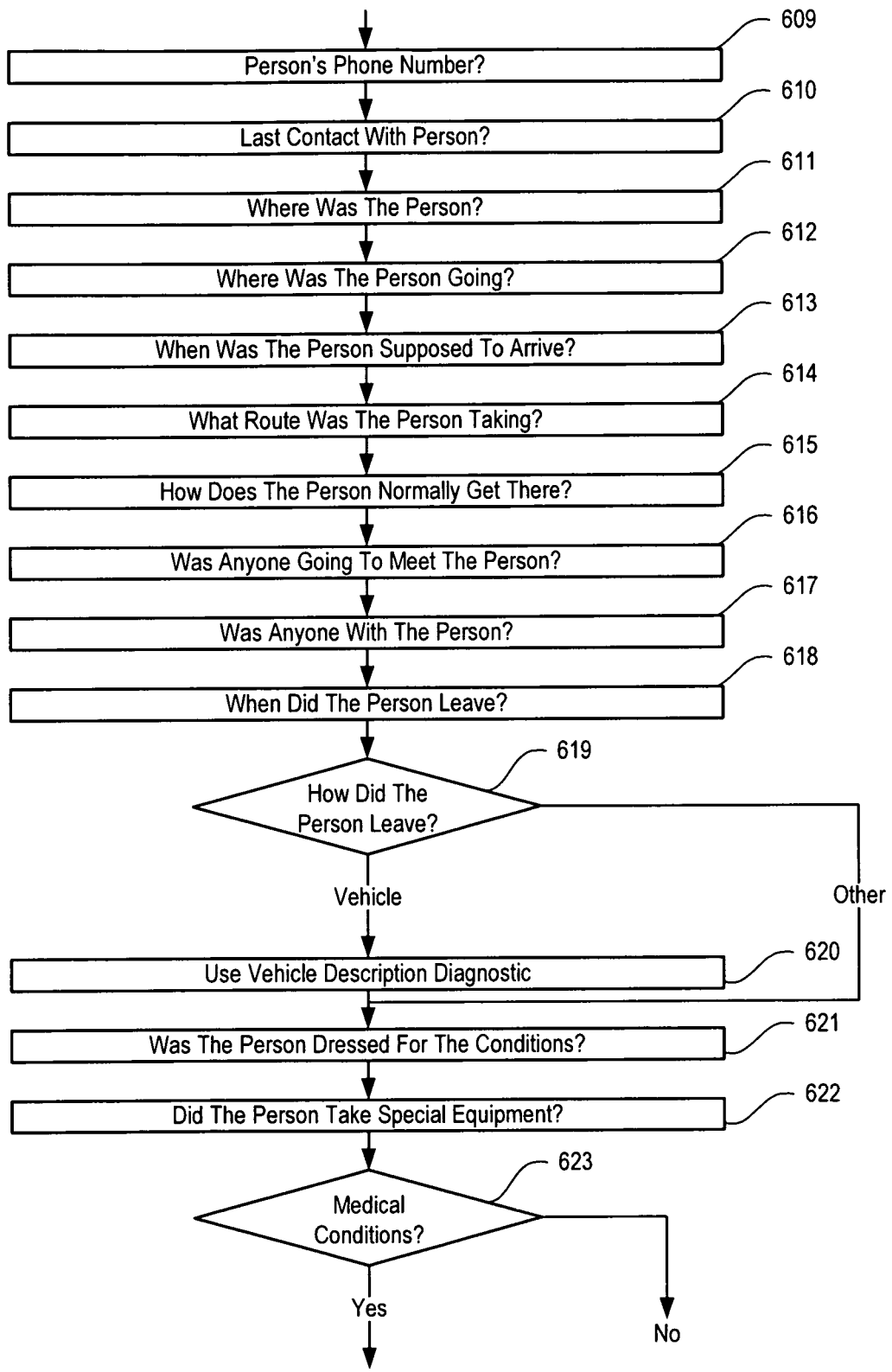
Figure 5C:
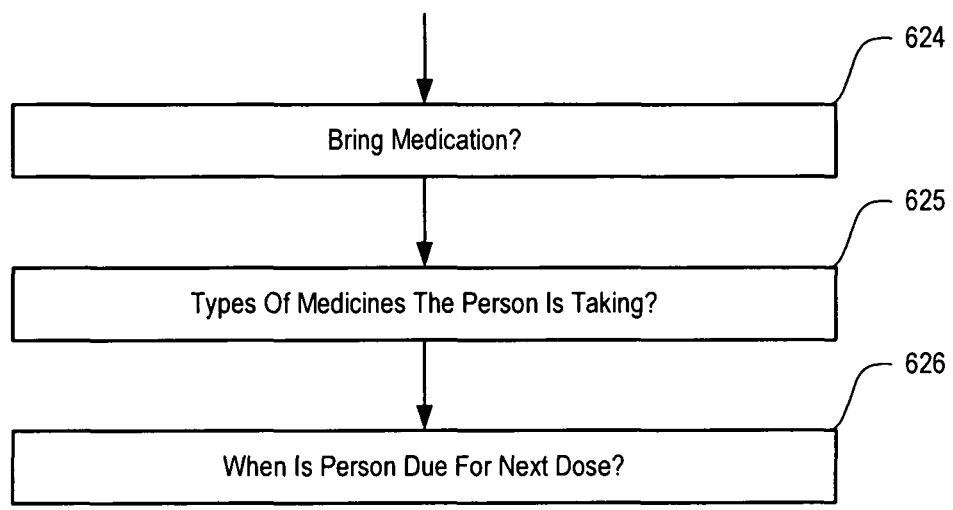

FIGS. 5A-C are a detailed flow diagram of a method 600 implemented by an emergency dispatch system including a locator diagnostic tool 122 (FIG. 1), according to one embodiment. The method 600 may be a variant for third party callers. A separate logical tree may be used by the locator diagnostic tool 122 if a third party caller is indicated, and/or different paths on the same logical tree may be used for first party versus third party callers.

The emergency dispatch system may begin by presenting 601 a preprogrammed inquiry, "What's the address of your emergency?" The user interface may include a freeform text box to receive input indicating the response, and/or the user interface may provide one or more possible selections. In response to the inquiry, the caller 118 may reply that the caller 118 "doesn't know," "can't say," and/or is otherwise unsure of the incident location. If the input indicates the incident location is not known, the emergency dispatch system may determine that the locator diagnostic tool 122 should be started.

Before starting the locator diagnostic tool 122, the emergency dispatch system may gather more basic information from the caller 118. The emergency dispatch system may present 602 a preprogrammed inquiry, "What's the phone number you're calling from?" A freeform text box may be provided to receive the response. The emergency dispatch system may present 603 a preprogrammed inquiry, "What's your name?" The emergency dispatch system may accept a freeform text response. The dispatcher 104 may also be presented 604 a preprogrammed inquiry, "Okay, tell me exactly what happened." The emergency dispatch system may accept freeform text and/or may include a plurality of predetermined possible incident types.

Once any additional information has been gathered, the emergency dispatch system may start 605 the locator diagnostic tool 122. The locator diagnostic tool 122 may present 606 a preprogrammed inquiry, "Does s/he have any (other) significant medical conditions?" The dispatcher 104 may be able to input a freeform text response. The locator diagnostic tool 122 may present 607 a preprogrammed inquiry, "What's her/his name?" Once the dispatcher 104 has input the person's name, the locator diagnostic tool 122 may launch 608 a person description diagnostic to get additional details about the person. When the person description diagnostic is complete, the locator diagnostic tool 122 may present 609 a preprogrammed inquiry, "What's her/his phone number (cell and house phone)?" The user interface of the locator diagnostic tool 122 may include freeform text boxes to receive the cell and house phone numbers.

The locator diagnostic tool 122 may ask questions designed to get additional details about where a missing person may be. For example, the locator diagnostic tool 122 may present 610 a preprogrammed inquiry, "When was the last time you had contact with her/him?" The dispatcher 104 may also be presented 611 a preprogrammed inquiry, "Where was s/he?" and present 612 a preprogrammed inquiry, "Where was s/he going (clarify place, address, phone)?" The user interface of the locator diagnostic tool 122 may present freeform text boxes to receive the responses to each inquiry, including boxes for the name, address, and phone number of the destination. The locator diagnostic tool 122 may present 613 a preprogrammed inquiry, "When was s/he supposed to be there (time, appointment, shift start)?" The dispatcher 104 may be able to input a freeform text indication of the time.

Additional questions may be designed to gather leads for responders searching for the missing person. The locator diagnostic tool 122 may provide 614 a preprogrammed inquiry, "What route was s/he taking?" and provide 615 a preprogrammed inquiry, "How does s/he normally get there?" Responders may be able to use the route information provided to begin searching along the route for the missing person. The locator diagnostic tool 122 may also present 616 a preprogrammed inquiry, "Was anyone going to meet her/him?" and present 617 a preprogrammed inquiry, "Was anyone or any pets with her/him?" Responders may be able to interview any individuals who had more recent contact with the missing person to obtain better leads on the missing person's possible whereabouts. The user interface may provide freeform text boxes to receive the responses to the additional questions.

The locator diagnostic tool 122 may present 618 a preprogrammed inquiry, "When did s/he leave (start)?" The dispatcher 104 may also be presented 619 a preprogrammed inquiry, "How did s/he leave (on foot, animal, boat, vehicle: car, bus, train, motorcycle, bike)?" If the missing person left in a vehicle, the locator diagnostic tool 122 may launch 620 a vehicle description diagnostic to obtain a description of the vehicle. Responders may use the start time and method of travel to determine a search radius and/or likely routes traveled by the missing person. The vehicle description may also allow alerts to be put out and aid responders in recognizing the missing person.

The locator diagnostic tool 122 may ask additional questions to determine what condition the missing person might be in and/or how urgent of a response is needed. The locator diagnostic tool 122 may present 621 a preprogrammed inquiry, "Was s/he dressed and prepared for the conditions?" Also, the locator diagnostic tool 122 may present 622 a preprogrammed inquiry, "Did s/he take any special equipment with her/him?" The user interface of the locator diagnostic tool 122 may provide preprogrammed responses of "Yes" and "No" to the inquiries about proper clothing and special equipment.

The locator diagnostic tool 122 may determine 623 if the missing person has any significant medical conditions. If the caller 118 had previously indicated that the missing person does not have serious medical conditions, the locator diagnostic tool 122 may automatically end and/or allow the dispatcher 104 to manually end the locator diagnostic tool 122. Otherwise, the locator diagnostic tool 122 may provide 624 a predetermined inquiry, "Did s/he take her/his medications with her/him?" The locator diagnostic tool 122 may present predetermined responses of "Yes" and "No" to the dispatcher 104. The locator diagnostic tool 122 may present 625 a predetermined inquiry, "What type of medicines are they?" The locator diagnostic tool 122 may allow a freeform text response to be input by the dispatcher 104. The dispatcher 104 may be presented 626 a predetermined inquiry, "When is s/he due for her/his next does?" The user interface may present a freeform text box to receive the response from the dispatcher 104.

After gathering information about medicines, the locator diagnostic tool 122 may automatically end and/or may allow the dispatcher 104 to manually end the locator diagnostic tool 122. When the locator diagnostic tool 122 ends, it may save all responses input by the dispatcher 104 so that the responses can be retrieved later, for example, while searching for the missing person. The locator diagnostic tool 122 may also provide post-dispatch instructions when it ends, such as, "Call anyone else you can think of that might know something. Call us back immediately if s/he contacts you or you get any more information. If s/he calls you, keep her/him on the line and call us from another phone if at all possible. We're walkin' the trail to find her/him now." The emergency dispatch system may return to the emergency dispatch protocol 108 when the locator diagnostic tool 122 ends.

FIG. 6 is a user interface 700 of a locator diagnostic tool 122 for an emergency dispatch system. In the embodiment shown, the locator diagnostic tool 122 is part of an option in a larger diagnostic tool. The larger diagnostic tool can be formed from a series of panels 702, 704 and 706. A home panel 702 can be used to select different subject matters, such as situations (e.g., urgent disconnect, critical caller danger, cord danger, monitor baby or mother, control bleeding, seizures, etc.). In addition, an estimated age of a caller 118 or victim 117 can be entered (e.g., adult, child, infant, or newborn). A protocol subpanel 704 can be used to select a protocol to aid the caller 118. In the example shown, the locator diagnostic tool 122 is activated by selection 708 of "Locator Diagnostic" by a dispatcher 104. In some embodiments, an information subpanel 706 is specific to each tool in the protocol subpanel 704.

When "Locator Diagnostic" is selected, the information subpanel 706 can be presented to the dispatcher 104. The information subpanel 706 can provide prompts to the dispatcher 104 for seeking more information from the caller 118. If information is received from the caller 118, the dispatcher 104 can click (or use a keyboard shortcut) to select the information type and enter the caller's descriptions. These descriptions can be forwarded and/or transmitted to emergency responder equipment for use by emergency responders.

The user interface 700 of the locator diagnostic tool 122 allows a dispatcher 104 to interface with the locator diagnostic tool 122. For example, the dispatcher 104 can ask the caller 118 about landmark information. The caller 118 can respond with a description of buildings, hills and/or trees. The dispatcher 104 can click on "Landmark info" within panel 706. An entry field can be presented to the dispatcher 104 for entry of the caller's description. The dispatcher 104 can then save the entry and return to the user interface 700. This process of prompting the caller 118 for information, clicking on an information category, entering information, and saving the entry can be repeated.

In other embodiments, an alternative user interface of the locator diagnostic tool 122 presents a pre-scripted interrogation, traversing one path of a logical tree. This alternative user interface of the locator diagnostic tool 122 allows a dispatcher 104 to interface with the locator diagnostic tool 122 and display results of the branching paths and/or receive further input to traverse further down the logical tree. Examples of a logical tree can be seen in conjunction with FIGS. 4A-4Q.

While specific embodiments and applications of the disclosure have been illustrated and described, it is to be understood that the disclosure is not limited to the precise configuration and components disclosed herein. Various modifications, changes, and variations apparent to those of skill in the art may be made in the arrangement, operation, and details of the methods and systems of the disclosure without departing from the spirit and scope of the disclosure.

What is claimed is:

1. A computer-implemented method to assist a dispatcher when communicating with a caller via telephone regarding an incident requiring an emergency dispatch response, the computer-implemented method comprising:
    presenting, on a dispatch center computer, a plurality of pre-scripted interrogatories for the dispatcher to ask the caller to collect information regarding the incident;
    receiving, on the dispatch center computer, input representative of the collected information;
    determining automatically on the dispatch center computer a determinant value indicative of priority of the incident from one of a plurality of pre-established determinant values based on the collected information;
    providing the determinant value from the dispatch center computer to a computer aided dispatch system;
    initiating a diagnostic tool on the dispatch center computer;
    the diagnostic tool presenting to the dispatcher a user interface;
    the user interface providing a plurality of pre-scripted location questions for the dispatcher to relay to the caller over the telephone to guide the caller in describing caller location information, wherein the diagnostic tool is configured to traverse a logical tree to determine which of the plurality of pre-scripted location questions will be relayed to the caller;

the user interface receiving dispatcher-entered input indicative of caller location information relayed from the caller, wherein the caller relays observations over the telephone to the dispatcher, and wherein the logical tree is traversed based on the dispatcher-entered input, the diagnostic tool storing the dispatcher-entered input for later recall;

providing the caller location information to the computer aided dispatch system;

the computer aided dispatch system receiving location and availability information from a plurality of emergency response unit devices corresponding to a plurality of emergency response units;

the computer aided dispatch system automatically dispatching at least one of the plurality of emergency response units based on the determinant value, the location and availability information received from the plurality of emergency response unit devices, and the caller location information received from the dispatch center computer;

the diagnostic tool prompting the dispatcher to ask the caller if the caller hears a siren of an emergency response unit;

upon receiving confirmation that the caller hears a siren, the diagnostic tool displaying instructions for the dispatcher to relay to the caller to assist emergency responders in locating the caller, the instructions including actions to make the caller seen or heard by the emergency responders; and upon receiving confirmation that the caller does not hear a siren, the diagnostic tool providing an option for the dispatcher to end the diagnostic tool.

2. The computer-implemented method of claim 1, further comprising the dispatch center computer initiating the diagnostic tool based on dispatcher-entered input indicative of one or more responses of the caller to the interrogatories presented to the dispatcher by the protocol.

3. The computer-implemented method of claim 2, wherein the dispatcher-entered input comprises an indication that the location of the caller is unknown.

4. The computer-implemented method of claim 1, wherein the logical tree comprises a first path traversed if the caller indicates the location of the caller is in an urban area and a second path traversed if the caller indicates the location of the caller is in a wilderness area.

5. The computer-implemented method of claim 1, wherein the logical tree comprises a first path traversed if the caller indicates the location of the caller is inside and a second path traversed if the caller indicates the location of the caller is outside.

6. The computer-implemented method of claim 5, wherein the logical tree comprises a third path traversed if the caller indicates the location of the caller is underground.

7. The computer-implemented method of claim 1, wherein the logical tree comprises a first path traversed if the caller is at a location of the incident and a second path traversed for missing third parties.

8. The computer-implemented method of claim 1, further comprising the diagnostic tool providing an instruction to the dispatcher to convey to the caller to determine the location of the caller, the instruction selected from the group consisting of activating a vehicle locator, activating an emergency pendant, calling from another phone, finding a piece of mail with an address, and attracting the attention of another person.

9. The computer-implemented method of claim 1, wherein the logical tree comprises a first path traversed if the caller can answer appropriately and a second path traversed if the caller is prevented from speaking.

10. The computer-implemented method of claim 1, further comprising the diagnostic tool providing an instruction to the dispatcher to convey to the caller if the caller is prevented from speaking, the instruction comprising an explanation of nonverbal signal types to the caller and a request to indicate a signal.

11. The computer-implemented method of claim 1, further comprising the diagnostic tool providing an instruction to the dispatcher to evaluate and input the caller's talking status.

12. The computer-implemented method of claim 1, wherein upon receiving confirmation that the caller hears a siren, the diagnostic tool prompting the dispatcher to ask the caller the direction of the siren.

13. A computer system to perform a method to assist a dispatcher when communicating with a caller via telephone regarding an incident requiring an emergency dispatch response, the computer system comprising:

a communication interface configured to communicate with a computer aided dispatch system in communication with a plurality of emergency response unit devices corresponding to a plurality of emergency response units;

a processor;

an output device in electrical communication with the processor;

an input device in electrical communication with the processor;

a memory in electrical communication with the processor, the memory comprising:

an emergency dispatch protocol including a plurality of pre-scripted interrogatories for the dispatcher to ask the caller to generate an emergency dispatch response;

the emergency dispatch protocol configured to determine automatically on the computer system a determinant value from one of a plurality of pre-established determinant values based on input representative of responses by the caller to one or more of the plurality of pre-scripted interrogatories;

the communication interface configured to provide the determinant value indicative of priority of the incident to the computer aided dispatch system; and a diagnostic tool to assist the dispatcher in guiding the caller, wherein the diagnostic tool performs the method of:

providing a plurality of pre-scripted location questions for the dispatcher to relay to the caller over the telephone to guide the caller in describing a physical environment, wherein the diagnostic tool is configured to traverse a logical tree to determine which of the plurality of pre-scripted location questions will be relayed to the caller;

receiving a plurality of input components associated with the plurality of pre-scripted location questions, the input components to receive dispatcher-entered input indicative of caller-relayed information concerning the physical environment, of the location of the caller, wherein the caller-relayed information is relayed over the telephone to the dispatcher, and wherein the logical tree is traversed based on the dispatcher-entered input;

prompting the dispatcher to ask the caller if the caller hears a siren of an emergency response unit;

receiving confirmation that the caller hears a siren;

displaying instructions for the dispatcher to relay to the caller to assist emergency responders in locating the caller, the instructions including actions for the caller to be seen or heard by emergency responders; and wherein the communication interface is configured to convey the information concerning the physical environment of the location of the caller to the computer aided dispatch system; and wherein the computer aided dispatch system is configured to automatically dispatch at least one of the plurality of emergency response units based on the determinant value, location and availability information received from the plurality of emergency response unit devices, and the information concerning the physical environment of the location of the caller.

14. The computer system of claim 13, wherein the logical tree comprises a first path traversed if the caller indicates the location of the caller is in an urban area and a second path traversed if the caller indicates the location is in a wilderness area.

15. The computer system of claim 13, wherein the logical tree comprises a first path traversed if the caller indicates the location of the caller is inside and a second path traversed if the caller indicates the location is outside.

16. The computer system of claim 15, wherein the logical tree comprises a third path traversed if the caller indicates the location of the caller is underground.

17. The computer system of claim 13, wherein the logical tree comprises a first path traversed if the caller is at a location of the incident and a second path traversed for missing third parties.

18. The computer system of claim 13, wherein the user interface further comprises an instruction to the dispatcher to convey to the caller to determine the location of the caller, the instruction selected from the group consisting of activating a vehicle locator, activating an emergency pendant, calling from another phone, finding a piece of mail with an address, and attracting the attention of another person.

19. The computer system of claim 13, wherein the logical tree comprises a first path traversed if the caller can answer appropriately and a second path traversed if the caller is prevented from speaking.

20. The computer system of claim 13, wherein the user interface further comprises an instruction to the dispatcher to convey to the caller if the caller is prevented from speaking, the instruction comprising an explanation of nonverbal signal types to the caller and a request to indicate a signal.

21. The computer system of claim 13, wherein the user interface further comprises an instruction to the dispatcher to evaluate and input the caller's talking status.

22. The computer system of claim 13, wherein upon receiving confirmation that the caller hears a siren, the diagnostic tool prompting the dispatcher to ask the caller the direction of the siren.

23. A non-transitory computer-readable storage medium having stored thereon computer-readable instruction code that, when executed by a computing device, causes the computing device to perform a method to assist a dispatcher when communicating with a caller via telephone regarding an incident requiring an emergency dispatch response, the method comprising:

providing, on the computing device, an emergency dispatch protocol to assist the dispatcher, the protocol presenting a plurality of pre-scripted interrogatories for the dispatcher to ask the caller to collect information regarding the incident;

receiving, on the computing device, input representative of the collected information;

determining automatically on the computing device a determinant value indicative of priority of the incident from one of a plurality of pre-established determinant values based on the input representative of the collected information to one or more of the plurality of pre-scripted interrogatories;

providing the determinant value to a computer aided dispatch system in communication with a plurality of emergency response unit devices corresponding to a plurality of emergency response units, the computer aided dispatch system receiving location and availability information from the plurality of emergency response unit devices;

initiating a diagnostic tool on the computing device, the diagnostic tool configured to aid the dispatcher in guiding the caller to describe the location of the caller to which the emergency dispatch response should be directed;

the diagnostic tool presenting to the dispatcher a user interface comprising:

indications of a plurality of pre-scripted location questions for the dispatcher to relay to the caller over the telephone to guide the caller in describing a physical environment of the location of the caller, and a plurality of input components associated with the plurality of pre-scripted location questions;

the diagnostic tool receiving dispatcher-entered input via the input components of the user interface, the dispatcher-entered input indicative of caller-relayed information concerning the physical environment of the location of the incident, wherein the caller's observations are relayed over the telephone to the dispatcher, wherein the diagnostic tool is configured to traverse a logical tree to determine which of the plurality of pre-scripted location questions will be relayed to the caller based on the dispatcher-entered input for previous questions; and the computing device providing the information concerning the physical environment of the location of the caller to the computer aided dispatch system, the computer aided dispatch system automatically dispatching at least one of the plurality of emergency response units based on the determinant value, the location and availability information received from the plurality of emergency response unit devices, and the information concerning the physical environment of the location of the caller received from the computing device;

the diagnostic tool prompting the dispatcher to ask the caller if the caller hears a siren of an emergency response unit;

upon receiving confirmation that the caller hears a siren, the diagnostic tool displaying instructions for the dispatcher to relay to the caller to assist emergency responders in locating the caller, the instructions including actions to make the caller seen or heard by the emergency responders; and upon receiving confirmation that the caller does not hear a siren, the diagnostic tool providing an option for the dispatcher to end the diagnostic tool.

* * * * *